US012125585B2

(12) United States Patent
Tatonetti

(10) Patent No.: US 12,125,585 B2
(45) Date of Patent: Oct. 22, 2024

(54) LEVERAGING BLOCKCHAIN TO SECURE DIALYSIS COMPONENTS AND MAINTAIN OPERATIONAL LOGS

(71) Applicant: KATA Gardner Technologies, Brooklyn, NY (US)

(72) Inventor: Thomas Tatonetti, Brooklyn, NY (US)

(73) Assignee: KATA Gardner Technologies, Brooklyn, NY (US)

(*) Notice: Subject to any disclaimer, the term of this patent is extended or adjusted under 35 U.S.C. 154(b) by 201 days.

(21) Appl. No.: 17/456,626

(22) Filed: Nov. 26, 2021

(65) Prior Publication Data

US 2022/0084666 A1  Mar. 17, 2022

(51) Int. Cl.
G16H 40/60 (2018.01)
G16H 10/60 (2018.01)
G16H 40/40 (2018.01)
G16H 50/20 (2018.01)

(52) U.S. Cl.
CPC ............ *G16H 40/40* (2018.01); *G16H 10/60* (2018.01); *G16H 40/60* (2018.01); *G16H 50/20* (2018.01)

(58) Field of Classification Search
None
See application file for complete search history.

(56) References Cited

U.S. PATENT DOCUMENTS

| 2018/0096121 A1* | 4/2018 | Goeringer | G06F 21/316 |
| 2019/0141048 A1* | 5/2019 | Fallah | H04L 9/0643 |
| 2019/0394050 A1* | 12/2019 | Goeringer | H04L 9/3263 |
| 2020/0349563 A1* | 11/2020 | Lu | G06Q 20/02 |
| 2020/0380482 A1* | 12/2020 | Hoffman | G06Q 20/02 |
| 2022/0168172 A1* | 6/2022 | Raheman | A61H 9/0092 |

FOREIGN PATENT DOCUMENTS

WO WO-2020197990 A1 * 10/2020 ............ G06F 21/64

* cited by examiner

*Primary Examiner* — John A Pauls
(74) *Attorney, Agent, or Firm* — Tatonetti IP

(57) ABSTRACT

A dialysis (e.g., hemodialysis or peritoneal dialysis) machine is instantiated with a blockchain application to help safeguard the machine from malicious attacks and provide a reviewable transaction log. The blockchain application may operate on a component level within a single dialysis machine or multiple dialysis machines that collectively operate within a blockchain community. Multiple rules and regulations may be utilized among the dialysis machines or dialysis machine components to ensure authorized instructions alter dialysis machine operations. The verification process can occur, for example, by discrete dialysis machine components verifying the instruction with a remote service or discrete dialysis machines verifying the instruction with the remote service. When a pre-set number of components or dialysis machines verify the instruction and develop a consensus, such as 50%, 75%, 90%, etc., the target component or machine executes the instruction.

20 Claims, 21 Drawing Sheets

1600

1700

1800

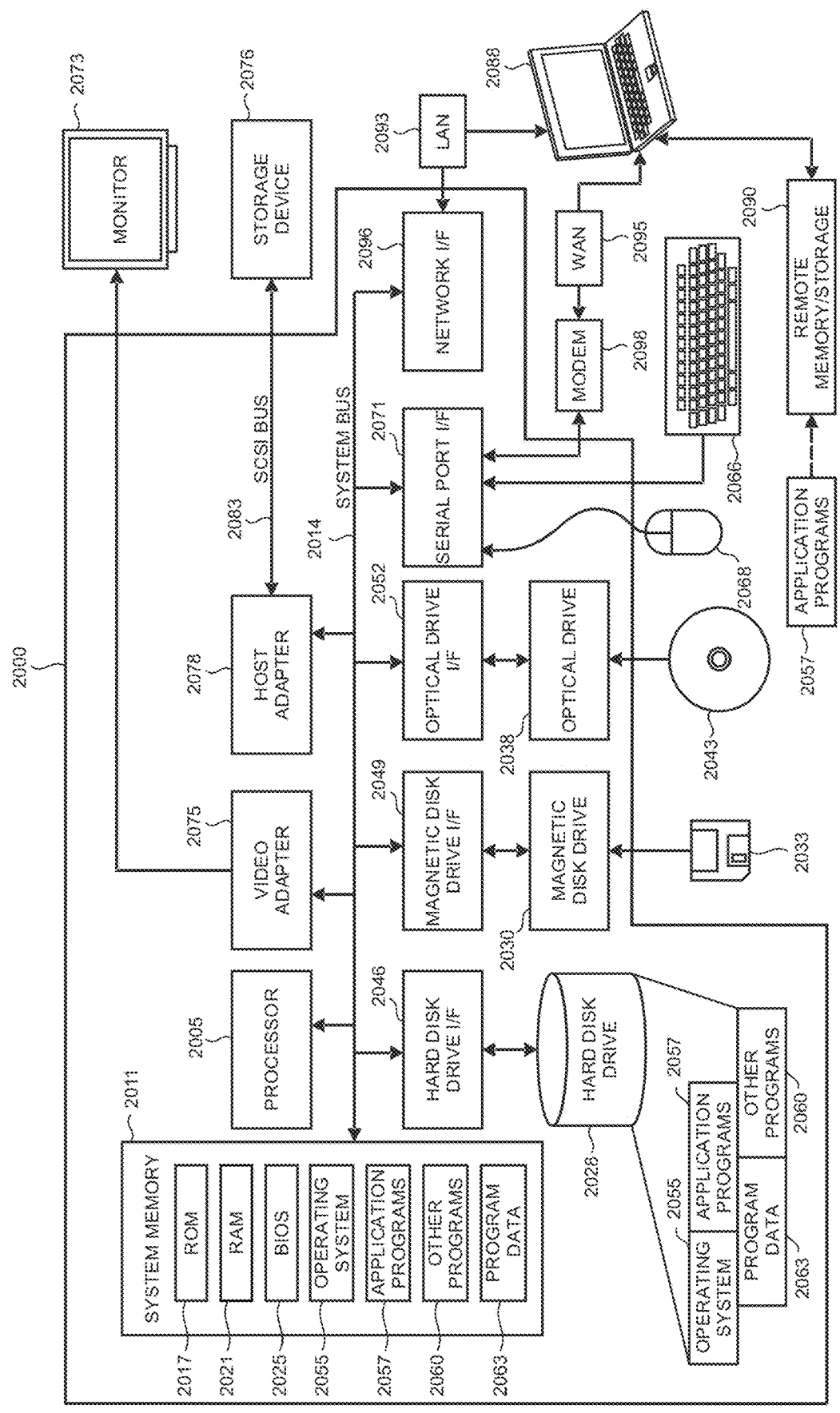

LEVERAGING BLOCKCHAIN TO SECURE DIALYSIS COMPONENTS AND MAINTAIN OPERATIONAL LOGS

BACKGROUND

Hemodialysis machines are utilized to filter a patient's blood due to renal failure, in which the dialysis machine utilizes numerous components and functions during filtration. The components and functionality of a given hemodialysis machine can vary by patient, such as the rate at which blood is pumped and the dialysate's composition, among other variances.

Whether it is a dialysis machine or other medical device, patients, medical professionals, governmental officials, and people at large worry the devices can be compromised by malicious actors, such as hackers, foreign governments, and other parties. For example, altering the functionality of a medical device could pose significant harm to the patient and, quite possibly, cause death.

SUMMARY

A dialysis (e.g., hemodialysis or peritoneal dialysis) machine or other medical device is instantiated with a blockchain application to help safeguard the device from malicious attacks and provide a reviewable transaction log. The blockchain application may operate on a component level within a single dialysis machine or multiple dialysis machines that collectively operate within a blockchain community. While dialysis machines are the primary example in the instant application, other medical devices configured with proper hardware as described herein can similarly implement and be protected using the described techniques.

The blockchain may be a public or private blockchain, depending on the implementation. Multiple rules and regulations may be utilized among the dialysis machines or dialysis machine components to ensure only authorized instructions alter dialysis machine operations. For example, in the component-level implementation, an instruction for a target component to alter operations within a dialysis machine may be verified by a pre-set number of other components before the target component can initiate the instruction. Similarly, in the dialysis-level implementation, multiple distinct dialysis machines can verify the authenticity of the instruction before the target dialysis machine can execute a machine modification.

The verification process can occur, for example, by discrete dialysis machine components verifying the instruction with a remote service, or discrete dialysis machines verifying the instruction with the remote service. When a pre-set number of components or dialysis machines verify the instruction and develop a consensus, such as 50%, 75%, 90%, etc., the target component or machine executes the instruction. Alternatively, notifications or commentary to a dialysis machine can likewise be verified beforehand to provide the user with additional security.

For the component level blockchain implementation, each component may be tied to a processor or a System on a Chip (SoC) that exercises control over the component. The blockchain application may be instantiated on each component's SoC. Typically, SoCs can be advantageous due to their cheap hardware, thereby giving greater control over each component and implementing a blockchain application.

An SoC may receive an instruction to modify its component's operation from a remote service or a computing device operated by a doctor. The SoC may transmit the instruction (such as by inputting the instruction in a created block) to multiple SoCs within the dialysis machine, which the components verify with the remote service or computing device. When a sufficient number of components develop a consensus for the instruction or the block's parameters, the target component executes the modification, and another block on the chain is added.

In some implementations, a token can be generated and passed among each component's SoC. The token is an indication for the respective SoC to check with a remote service for any instructions, or the token can itself include the instruction. Furthermore, each component is authorized to make a modification when their respective SoC holds the token or within a threshold period of time after receiving the token. All other dialysis machine components are unauthorized to modify its operations until it receives the token.

The token may come with an instruction for a machine modification. Each SoC that receives the token may verify the instruction with a remote service before the target component is authorized to make the change. When the token passes to the target component after a sufficient number of SoCs verified the instruction (e.g., 50%), that SoC may authorize the component modification. The token may be a basis for each component to generate a block on the chain.

Furthermore, an adapter may be plugged into existing medical devices to provide the disclosed blockchain security measures for older devices and/or streamline the technologies adaptation. The plugin may be a standalone hardware device that operates the blockchain application and stands between the dialysis machine (or other medical devices) and the remote service providing the instruction. Alternatively, the adapter may be a software application downloaded onto a medical device and likewise stands between the medical device's software and the remote service's instructions. That is, the adapter executes the blockchain application and prevents or authorizes the instruction to pass to the medical device after verification (e.g., the consensus among other devices).

While the instant disclosure may be tailored to hemodialysis machines, other medical devices can also implement the technology discussed herein. For example, peritoneal dialysis machines, pacemakers, vital signs monitors, local or remote computing devices operating in a medical office or hospital setting, among other devices, can implement the disclosed technology. The application of blockchain security to medical devices enables patients, doctors, medical workers, and families to have some assurances that a medical device dedicated to a specific patient is no longer standalone—it is connected and verified by multiple other machines. Even better, distinct machines may operate different security protocols developed by distinct security software (e.g., McAfee®, Norton®, Bitdefender®, etc.). If medical devices protected by different security software all verify a particular instruction, that leads to greater assurances that the instruction is authorized. That is, it's unlikely that a hacker comprised multiple different security software simultaneously. The blockchain's ledger also provides verified information to trace any suspicious activity.

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. It will be appreciated that the above-described subject matter may be implemented as a computer-controlled apparatus, a computer process, a computing system, or as an article of manufacture such as one or more computer-readable storage media. These and various other features will be apparent from reading the following Detailed Description and reviewing the associated drawings.

DESCRIPTION OF THE DRAWINGS

FIG. 20 is a simplified block diagram of an illustrative remote computing device, remote service, medical device, or computer system that may be used in part to implement the present leveraging blockchain to secure dialysis machine components.

Like reference numerals indicate like elements in the drawings. Elements are not drawn to scale unless otherwise indicated.

DETAILED DESCRIPTION

Figure 1:
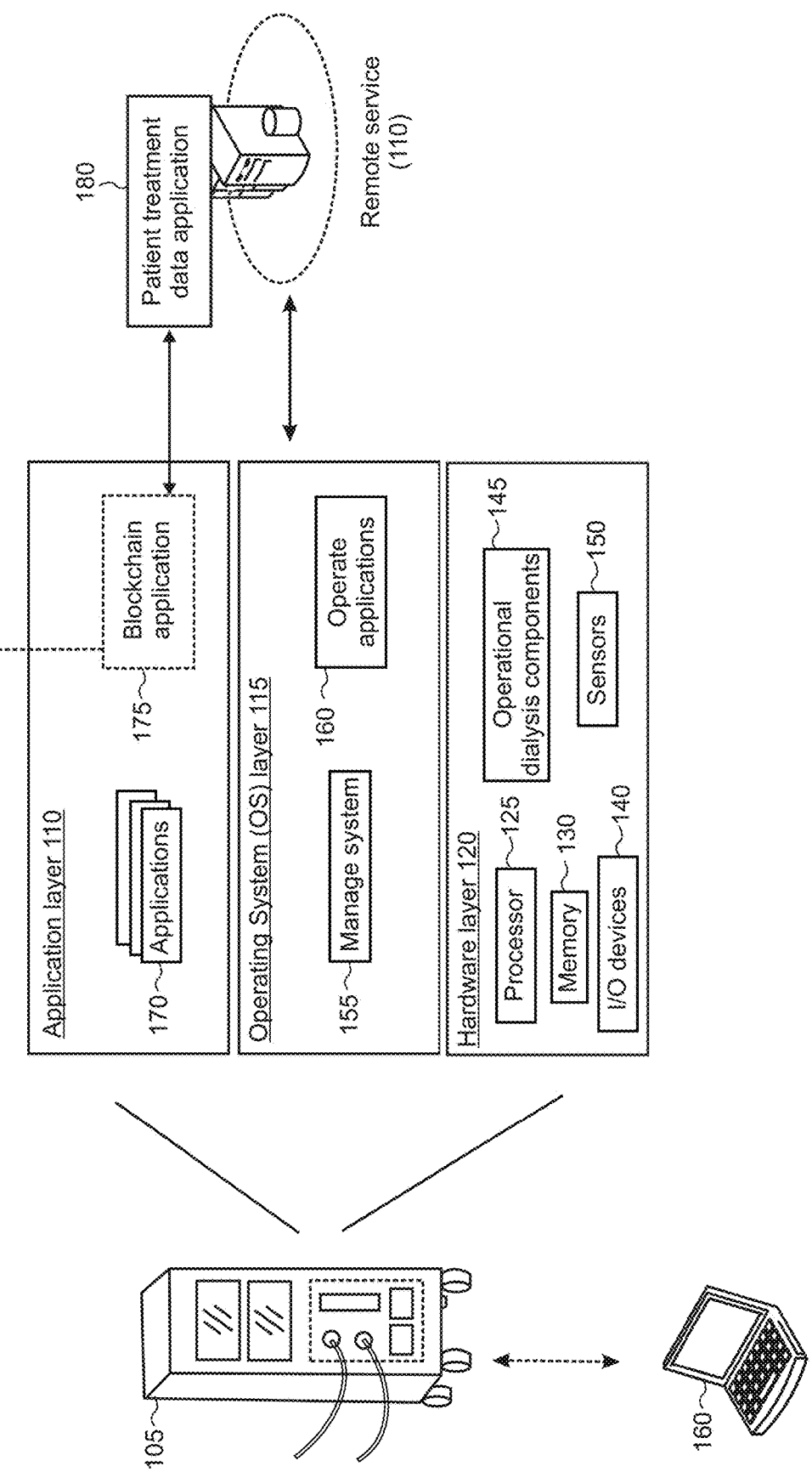
FIG. 1 shows an illustrative layered architecture of a hemodialysis machine.

FIG. 1 shows a simplified layered architecture 100 of the hemodialysis machine 105. The machine can include a hardware layer 120, operating system (OS) layer 115, and application layer 110. The hardware layer 115 provides an abstraction of the various hardware used by the hemodialysis machine 105 (e.g., input and output devices, networking and radio hardware, etc.) to the layers above it. In this illustrative example, the hardware layer supports processor(s) 125, memory 130, input/output devices (e.g., mouse, keyboard, display) 140, operational dialysis components 145, and sensors 150 for sensing operations of the hemodialysis machine (e.g., pump speed, blood or saline composition, etc.). A description of the operational dialysis components is discussed in greater detail with respect to FIG. 2. Although not shown, the hemodialysis machine can also include a network interface card (NIC) which enables a wired or wireless connection to the Internet, such as through a router. This can enable the hemodialysis machine to communicate with the remote service 110 (e.g., transmit data and feedback, receive settings and notifications, etc.). In some implementations, the hemodialysis machine can support short-range communications over Bluetooth® or NFC (Near Field Communication), such as to a user's computing device (e.g., smartphone, tablet computer, personal computer (PC), laptop, etc.).

The application layer 110 in this illustrative example supports various applications 170, including a blockchain application 175 that operates with other similar blockchain applications instantiated on distinct dialysis machines or dialysis machine components. The blockchain is a shared, immutable ledger that facilitates the process of recording transactions and tracking assets in a network. Depending on the implementation, the asset can be tangible (e.g., a house, car, cash, land) or intangible (intellectual property, patents, copyrights, branding). In this implementation, the asset may be instructions from a medical provider, such as a remote service or physician operating a computing device, to a hemodialysis machine, medical device, or computing device tied to a patient. Like other assets, the operational instruction (e.g., treatment instruction, dialysis machine modification, entire prescription, comment/notification, etc.) can be tracked on a blockchain network, reducing risk and enhancing security.

As each medical instruction to a dialysis machine occurs, the instruction is recorded as a "block" of data on the blockchain, which is individually maintained and verified by a plurality of other dialysis machines or medical devices. The blockchain can be a public or private blockchain. In a public blockchain network, anyone (or device) may be free to join and participate and is often referred to as permissionless. While private blockchain networks are typically known as permissioned networks, public blockchains may also be permissioned and have some rules for participants to join. As one example, a public blockchain network may restrict particular medical devices together, such as hemodialysis machines, peritoneal dialysis machines, vital signs monitors, pacemakers, etc. Other types of permissions for a blockchain network may be patient criteria (e.g., age, location, demographics, etc.).

The data block can record the medical instruction as well, such as who made the instruction (e.g., which doctor) and who the subject patient is, information about the medical device (e.g., make and model number and other operational components about the machine), what the instruction was (e.g., minor component modification or more substantial change that affects multiple components), when the instruction was transmitted and received, where the dialysis machine and associated patient is located (among other geographic data), etc. Such blocked information can be customized based on the proprietary design and customizations of the blockchain application 175. Each block may be created based on a given consensus protocol utilized by the blockchain application 175. Exemplary blockchain applications can include Proof of Work (PoW) 182, Proof of Stake (PoS) 184, Proof of Activity (PoA) 186, Practical Byzantine Fault Tolerance (PBFT) 188, and selective endorsement 190.

The specific consensus protocol depends on the implementation. For the present implementation, using a consensus protocol that quickly and efficiently creates the block may be ideal to avoid delay between the doctor's instruction and the device executing the instruction. For example, consensus may be developed in the instant application by checking the remote service 110 and potentially other computing devices (e.g., other remote services or computing devices not shown in FIG. 1) for the instructions veracity. Other devices on the chain can check the veracity of the instruction with the remote service to achieve consensus. No Proof of Work (PoW) to delay the instruction's application may be used in most implementations.

These transactions in the form of medical device treatment instructions are blocked together in an irreversible chain: a blockchain. Each additional block strengthens the verification of the previous block and hence the entire blockchain. This renders the blockchain tamper-evident for each computing (medical) device that analyzes the individual transactions blocks to achieve a consensus, thereby establishing immutability. This removes the possibility of tampering by a malicious actor—and builds a ledger of transactions that network members (e.g., machines, physicians, technicians, etc.) can trust. Furthermore, tying the medical device's implementation of the prescribed treatment instruction to the immutable ledger even further heightens the machine's security and provides peace of mind.

A private blockchain network, similar to a public blockchain network, is a decentralized peer-to-peer network. However, one defined organization governs the network in a private blockchain, thereby enabling control over who is allowed to participate (e.g., which medical devices are invited), execute a consensus protocol (e.g., PoW, PoS, etc.) and maintain the shared ledger. Depending on the use case, this can significantly boost trust and confidence between participants. A private blockchain can be run behind a corporate firewall and even be hosted on-premises, thereby providing even greater protection.

Although the various applications are depicted as stand-alone applications in FIG. 1, the applications may alternatively operate within the same application, as a plugin to other applications or the OS, or interoperate with remotely executing code, such as with the remote service 110. Although only certain applications are depicted in FIG. 1, the hemodialysis machine (or other medical devices) can utilize any number of applications. The applications are often implemented using locally executing code. In some cases, however, these applications can rely on services and/or remote code execution provided by remote servers or other computing platforms such as those supported by a service provider or other cloud-based resources (not shown).

The remote service 110 may host a patient treatment data application 180 that stores and manages various patient data. The patient treatment data application may be updated by a service provider (e.g., physician or nurse). For example, a provider at a physician's office may input patient data for storage in the remote service, and the patient's record may be periodically updated based on follow-up visits. For example, the patient treatment data application may store various patient information, such as visit dates, name, address, illnesses, symptoms, prescriptions, treatments, age, and other typical information in a patient's electronic medical record. As discussed in greater detail below, hemodialysis machines and their components and other medical devices can check with the remote service's patient information to achieve a consensus for an instruction to a target machine/device.

The blockchain application 175 and patient treatment data application 180 may be part of the same or different applications, but one or both may be referenced in an application programming interface (API) of the other. As discussed in greater detail below, operational instructions may be passed to the hemodialysis machine 105, but that instruction may first pass through the blockchain application for verification and security. Each hemodialysis machine operating on a given blockchain may use the blockchain application's features, as a plugin, adapter, or standalone application, to collaborate and establish consensuses for instructions. Thus, depending on the specific setup of the system, the remote service may be configured with the blockchain application, and created instructions may be checked within that application. Or, the blockchain applications may otherwise be configured to securely access a piece of the patient data to verify instructions.

The OS layer 115 supports, among other operations, managing system 155 and operating applications/programs 160. The OS layer may interoperate with the application and hardware layers in order to perform various functions and features.

Figure 2:
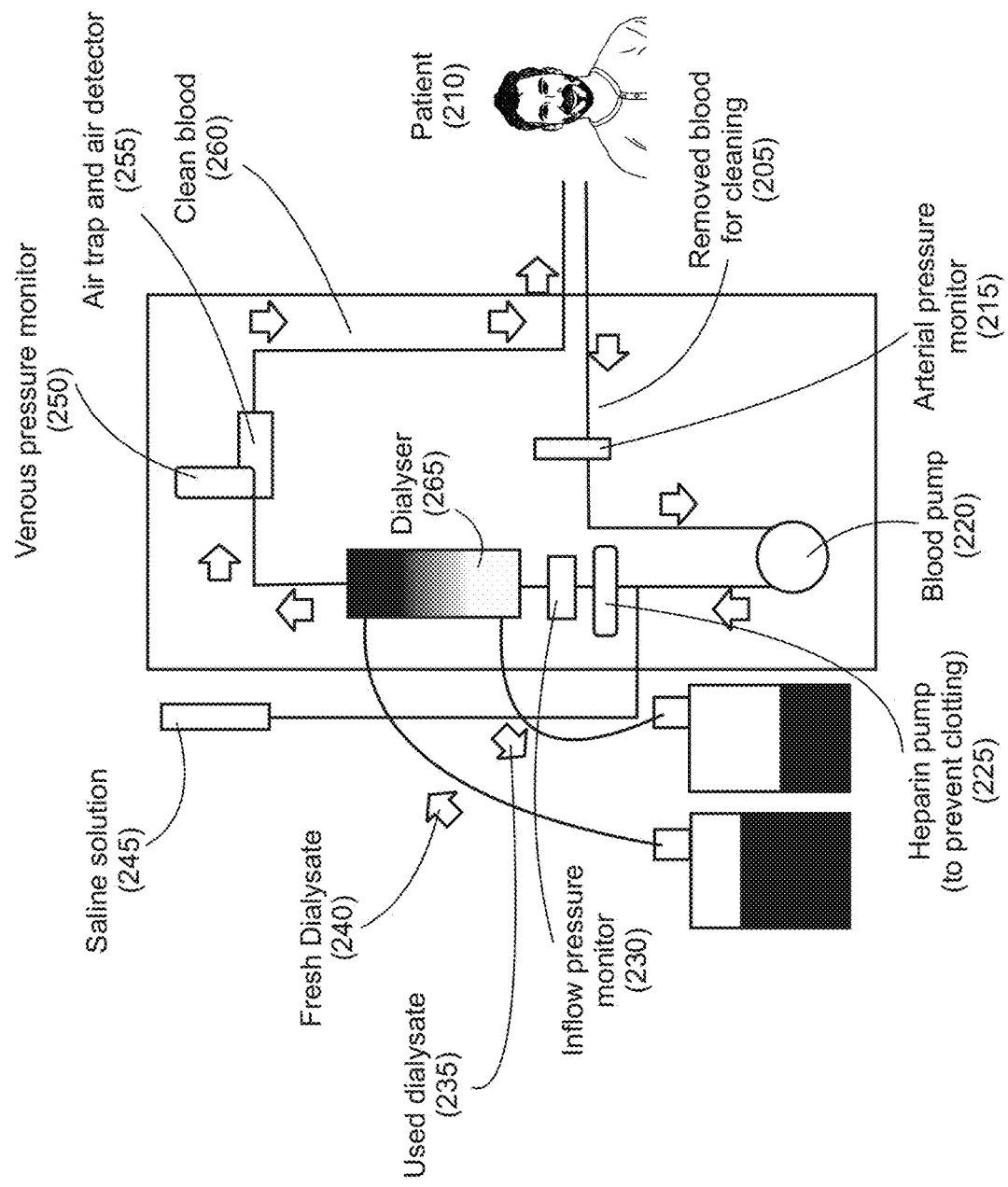
FIG. 2 shows an illustrative diagram of the hemodialysis machine's operational components.

FIG. 2 is an exemplary hemodialysis machine 200 which may be implemented and utilized for the purposes described herein. The diagram shows the various components and operations of the hemodialysis machine, but other components not shown are also possible. The hemodialysis machine uses the blood pump 220 to remove blood from patient 210, as representatively shown by numeral 205. An arterial pressure monitor 215 may be implemented to regulate the amount of pressure and ensure that excessive negative pressure is not generated. A heparin pump 225 injects a regulated amount of heparin into the blood within the tube while the patient is undergoing treatment. Heparin may be utilized to prevent blood clotting during treatment.

Before entering the dialyzer 265, the blood flows through an inflow pressure monitor 230 to regulate the inflow of blood. Saline solution 245 can be utilized to flush the system and cleanse the blood that is to be flowing back into the patient through the hemodialysis system. Next, the blood enters the dialyzer, which removes wastes like urea and adds sodium bicarbonate to correct blood acidity. The process by which the dialyzer purifies the blood for bodily use is diffusion, in which the artificial filter of the dialyzer employs fibers, dialysate, and a semi-permeable membrane through which the blood flows. Used dialysate 235 flows to a waste container, and fresh dialysate 240 is pulled into the dialyzer 265.

Once the blood advances through the dialyzer 265, a venous pressure monitor 250 may be utilized to measure the flow of cleansed blood through the user's vein and into the body. An air trap and air detector 255 are utilized to ensure no air enters the user's venous needle and vein when moving the cleansed blood back into the user's body. The clean blood 1560 then enters through the user's body through the final portion of the tube, through a needle, and into the user's vein.

Figure 3:
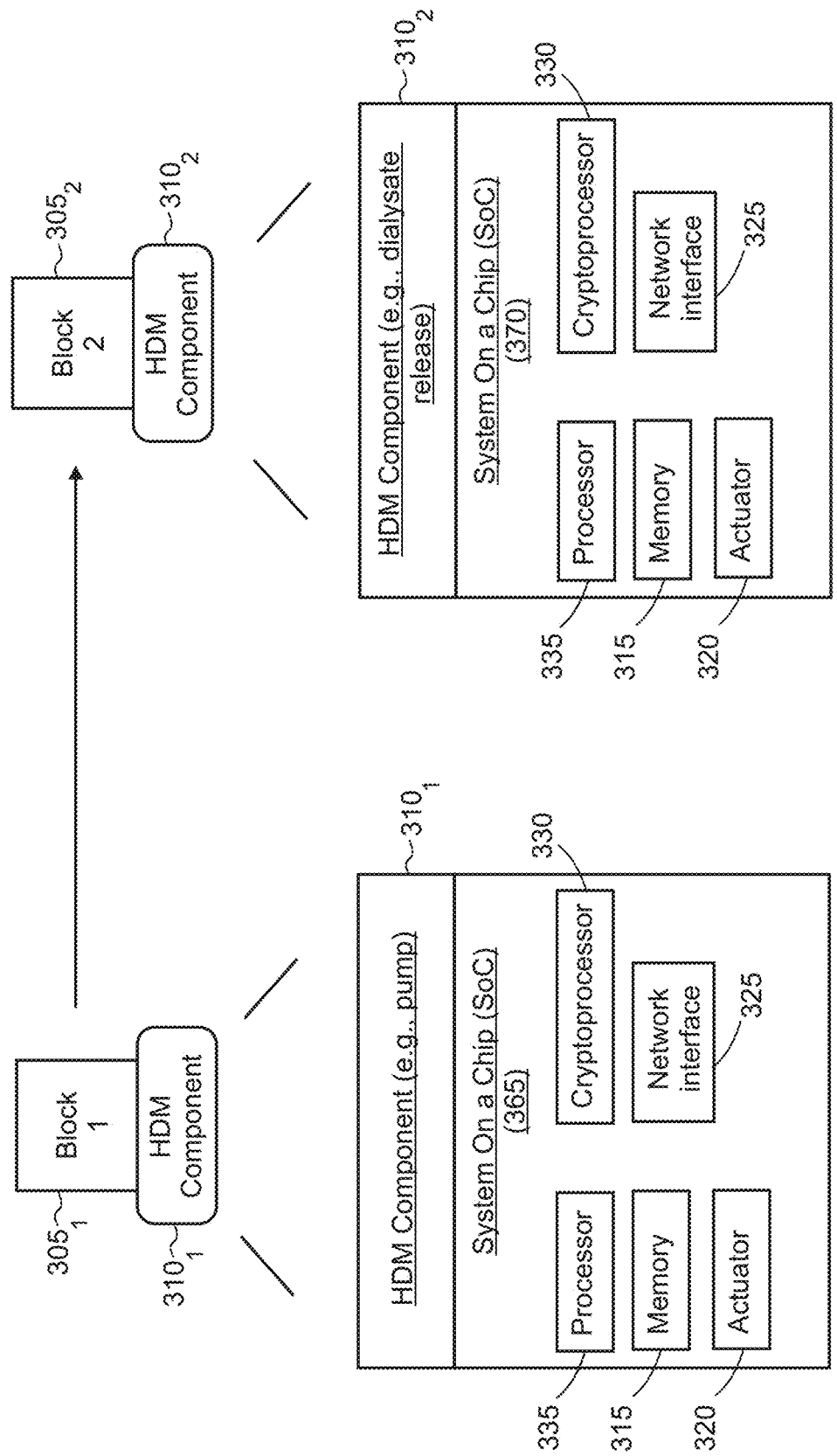
FIG. 3 shows an illustrative diagram of a System on a Chip (SoC) implementation with hemodialysis machine components.

FIG. 3 shows an illustrative representation of a System on a Chip (SoC) 365, 370 connected with each respective hemodialysis component 310. The SoCs may create blocks 305 in the blockchain and authorize any machine modifications at a hemodialysis machine. The processors 335 and memories 315 may be configured and operate similar to the processor and memory discussed above with respect to FIG. 1. The network interfaces 325 may be a network interface card (NIC) that supports wired (e.g., Ethernet) or wireless communications (e.g., WiFi, Bluetooth®, NFC (near-field communication), etc. The actuator 320 may be software- or hardware-driven and causes the dialysis machine component 310 to execute a modification responsive to instruction. The actuator may be a software instruction on the SoC and a hardware component that adjusts the operations of a given dialysis machine component. The dialysis machine's actuator may be standard for each component; the instant application is tailored to control authorization to the actuator.

The cryptoprocessors 330 may provide an additional security layer for the hemodialysis machine at large and its components. The cryptoprocessor may be configured with various tamper-resistant hardware and/or software to provide greater security to any component or machine modifications. The secure cryptoprocessor may not output decrypted data or decrypted program instructions in an environment where security cannot be maintained. In this regard, the cryptoprocessor may receive instructions from other cryptoprocessors, thereby enhancing security around the medical device's operations. Thus, the instant disclosure provides a blockchain implementation as a security measure, a secure cryptoproces sing environment as a security measure, and a combination of the two.

Figure 4:
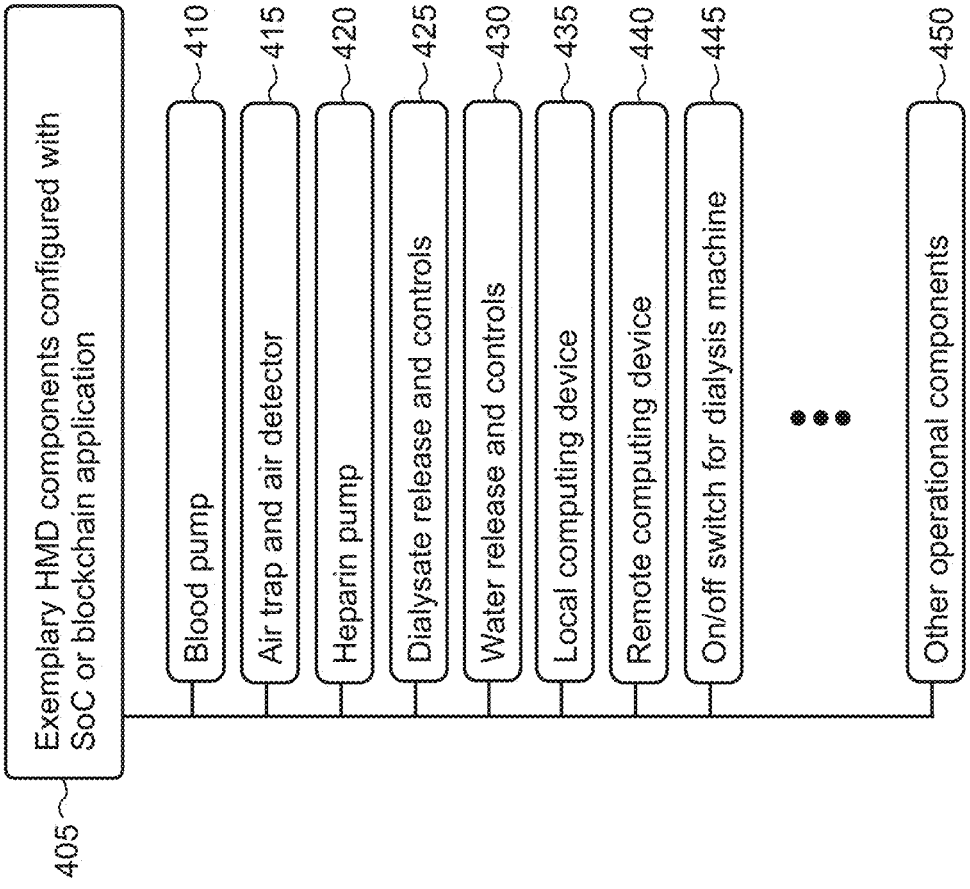
FIG. 4 shows an illustrative schema of hemodialysis machine components to which an SoC may be connected.

FIG. 4 shows an illustrative schema 400 of exemplary hemodialysis machine (HMD) components configured with an SoC or blockchain application, as representatively shown by numeral 405. Exemplary and non-exhaustive components or systems include the blood pump 410, air trap and air detector 415, heparin pump 420, dialysate release and controls 425, water release and controls 430, local computing device (e.g., laptop associated with the dialysis machine) 435, remote computing device (e.g., remote service associated with the dialysis machine) 440, on/off power switch for dialysis machine 445, and other operational components 450.

Figure 5:
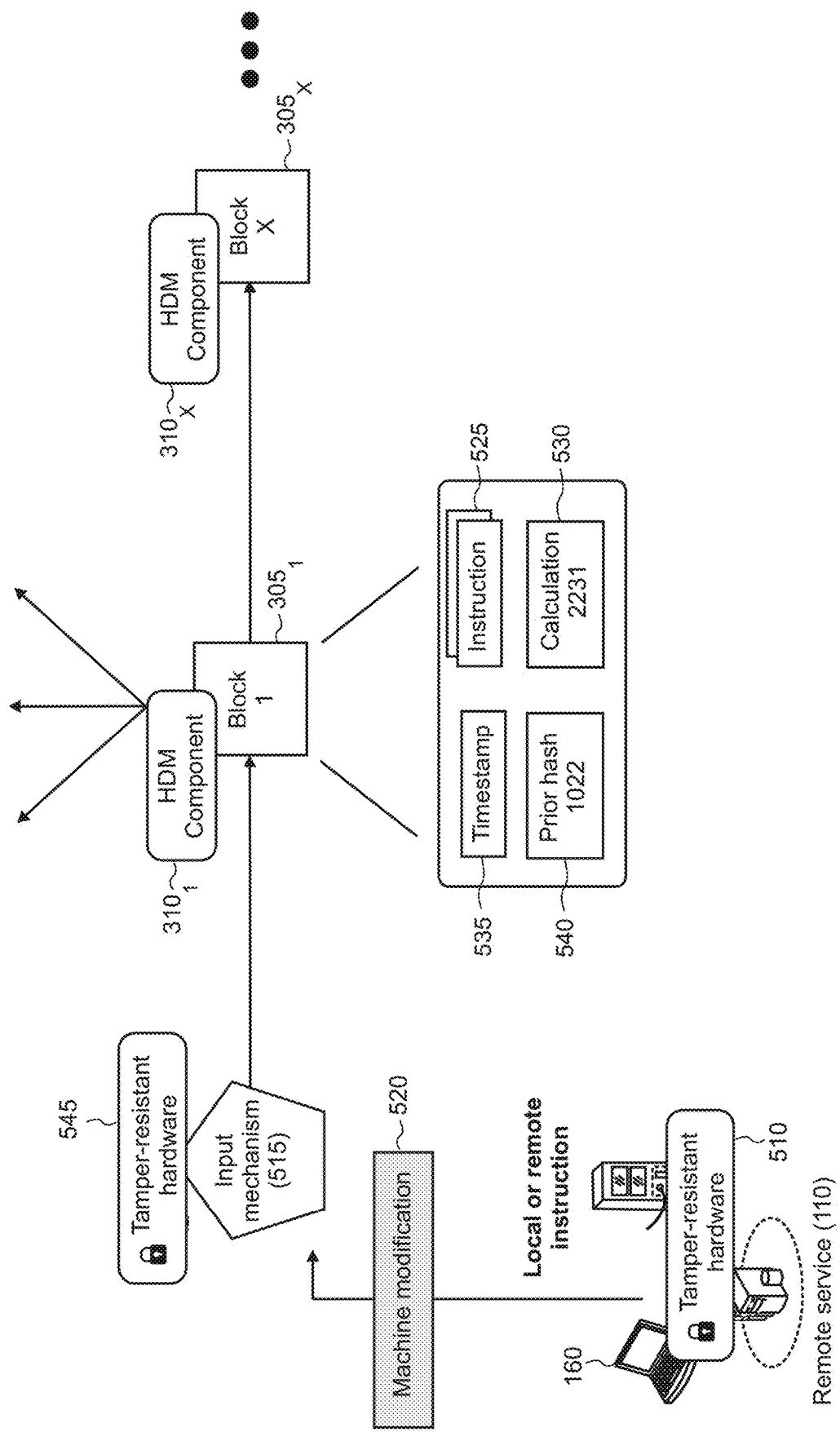
FIG. 5 shows an illustrative environment in which a machine modification instruction is transmitted to a component.

FIG. 5 shows an illustrative environment where a machine modification 520 is transmitted from a computing device 160 or remote service 110 to the hemodialysis machine 105 or directly into the hemodialysis machine 105. The instruction may be transmitted or input at the input mechanism 515 of the hemodialysis machine, which may be some input screen or a network interface that receives the instructions and transmits the instructions to its local processor. Alternatively, the input mechanism may serve as a security device before receiving any user-customized input. The security device may utilize a biometric scan (e.g., fingerprint, facial recognition, iris scan), PIN (personal identification number) code, alphanumeric password, etc.

The hemodialysis machine 105 may have a processor that processes the instruction or forwards the instruction to the target component's SoC. FIG. 5 shows that the transmitting component may utilize tamper-resistant hardware 510 and the dialysis machine utilized tamper-resistant hardware 545. The tamper-resistant hardware may be, for example, a cryptoprocessor, Trusted Platform Module (TPM), or otherwise configured with tamper-resistant protocols.

The machine modification 520 may be forwarded to the specific SoC associated with the hemodialysis machine component 310, which transmits the instruction to other components for consensus, as representatively illustrated by numeral 505. After a sufficient number of distinct components verify the instruction, such as by checking with a remote service that stores the instruction, the SoC for the HDM component 310 creates Block 1 (305) for the blockchain. The block includes a timestamp 535, the prior hash 540 (if present), the instruction 525, and the calculation 530 for that next specific block. The calculation may be based on some hash function using the prior hash. If no prior hash is present, this may be a genesis block (i.e., "Block 0"). This block is then transmitted to each of the components to provide an updated blockchain. FIG. 5 shows the subsequent block and HDM component in the chain with an "X" to illustrate the next block in the chain can be developed from Block 1.

Figure 6:
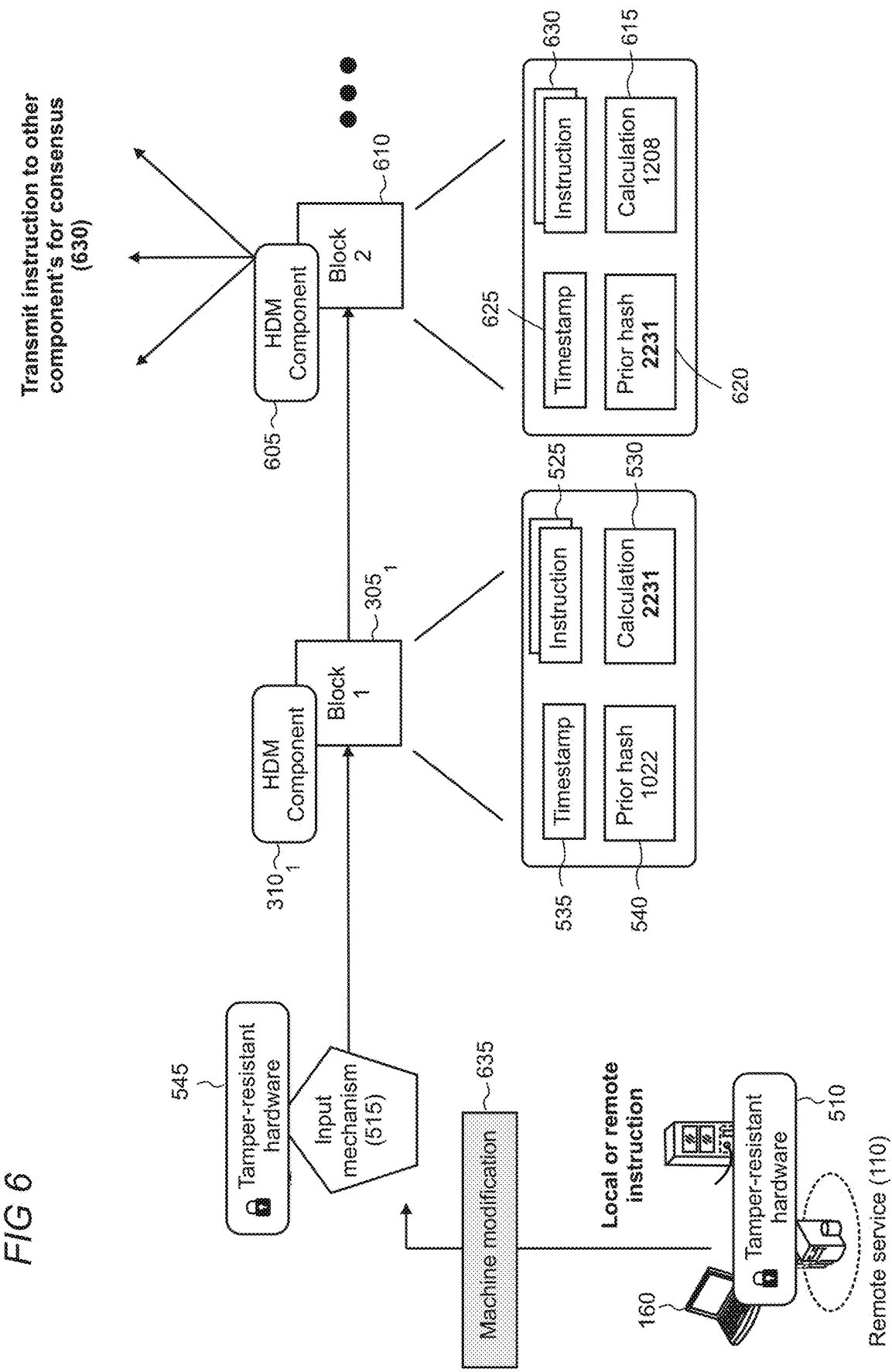
FIG. 6 shows an illustrative environment in which a subsequent instruction is received by another component in the hemodialysis machine.

FIG. 6 shows an illustrative subsequent modification instruction 610 transmitted from a computing device 160, remote service 110, or directly input into the hemodialysis machine 105 received at the input mechanism 515. Block 2 (610) is created from the SoC associated with HDM component 605 based on the received instruction for the machine modification. The HDM component 605 transmits the instruction to other HDM components for consensus, as representatively illustrated by numeral 630. Block 2 (610) is generated after a sufficient number of components verify and authenticate the instruction, such as by checking with a remote service or some computing device for the instruction. Block 2 includes a timestamp 625, instruction 630, prior hash 620, and calculation 615. As shown, the prior hash 620 is based on Block 1 (305). The calculation will be used in Block 3, and the blockchain continues as such.

Figure 7:
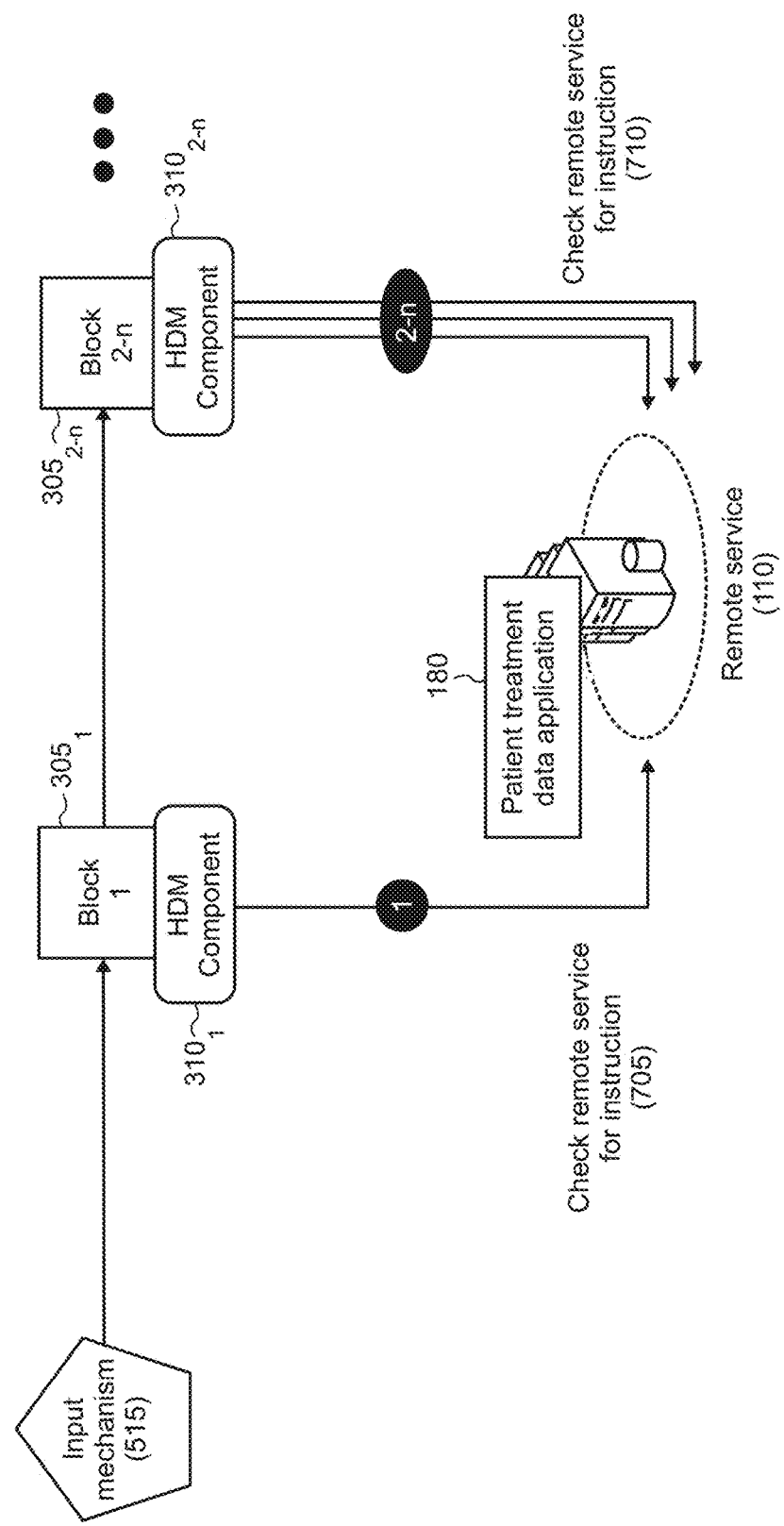
FIG. 7 shows an illustrative environment in which the hemodialysis machine components check a remote service for component instructions.

FIG. 7 shows an illustrative environment where the HDM components 310 check with the remote service 110 an instruction received at a specific component. The checking may be responsive to the given component transmitting the received instruction to each component, although not shown. This verification process may be performed by multiple or each dialysis machine component 2-n, representing each component after the first block. The first HDM component 310$_1$ may check the instruction as a baseline, and each or at least multiple other components may likewise check the instruction. These instructions may first be put inside a block created by the target component, in which the other components check the block's parameters.

The checking process may be a request from the component to the remote service's patient treatment application 180 for a given block or instruction. The patient treatment application can provide, such as by transmitting the instruction to the respective component, an instruction verification that matches the instruction at the target component. If the instruction provided is NIL or otherwise inaccurate, then the components won't approve the instruction for the consensus. The components can move toward the consensus if the received instruction corresponds to (matches or sufficiently matches) the instruction. Each component's SoC may perform a similar checking function, as shown by the "2-n" representation and the multiple lines. That is, multiple HDM components and SoCs may execute this check for the consensus, but only two devices are shown. Likewise, such a checking function may be performed for each block 2-n.

Figure 8:
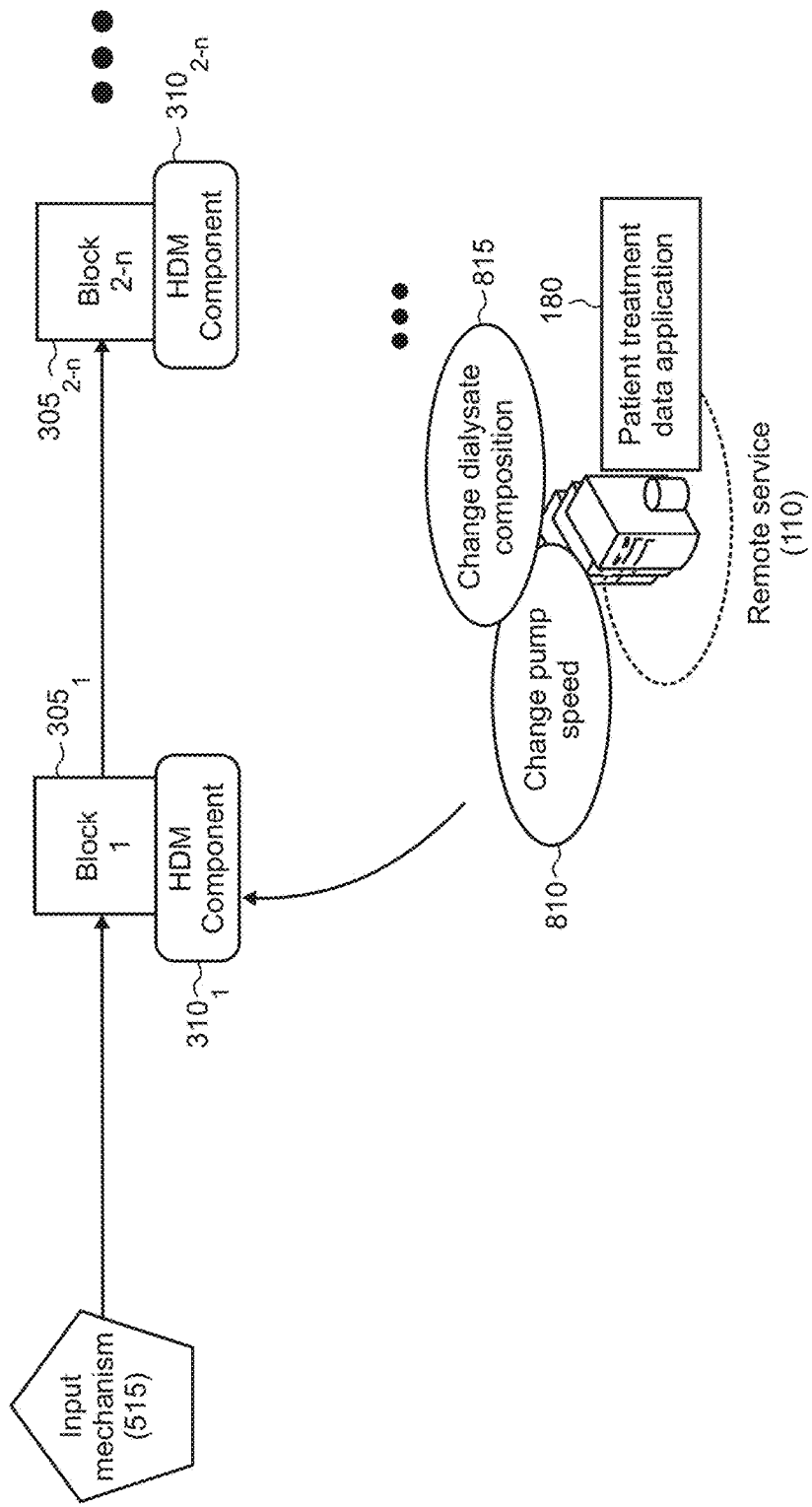
FIG. 8 shows an illustrative environment in which the hemodialysis machine component authorizes an instructional change in operation when sufficient components agree on the instruction.

FIG. 8 shows an illustrative representation in which the SoC associated with the hemodialysis machine component 310 modifies its operations when a pre-set percentage of components operating on the blockchain validate the instruction, as representatively illustrated by numeral 805. The modification can be, for example, a change in pump speed 810, change in dialysate composition 815, among other changes to components as illustrated by the ellipsis. The exemplary instructions shown may be the instructions that are checked by a consensus of machine components.

Figure 9:
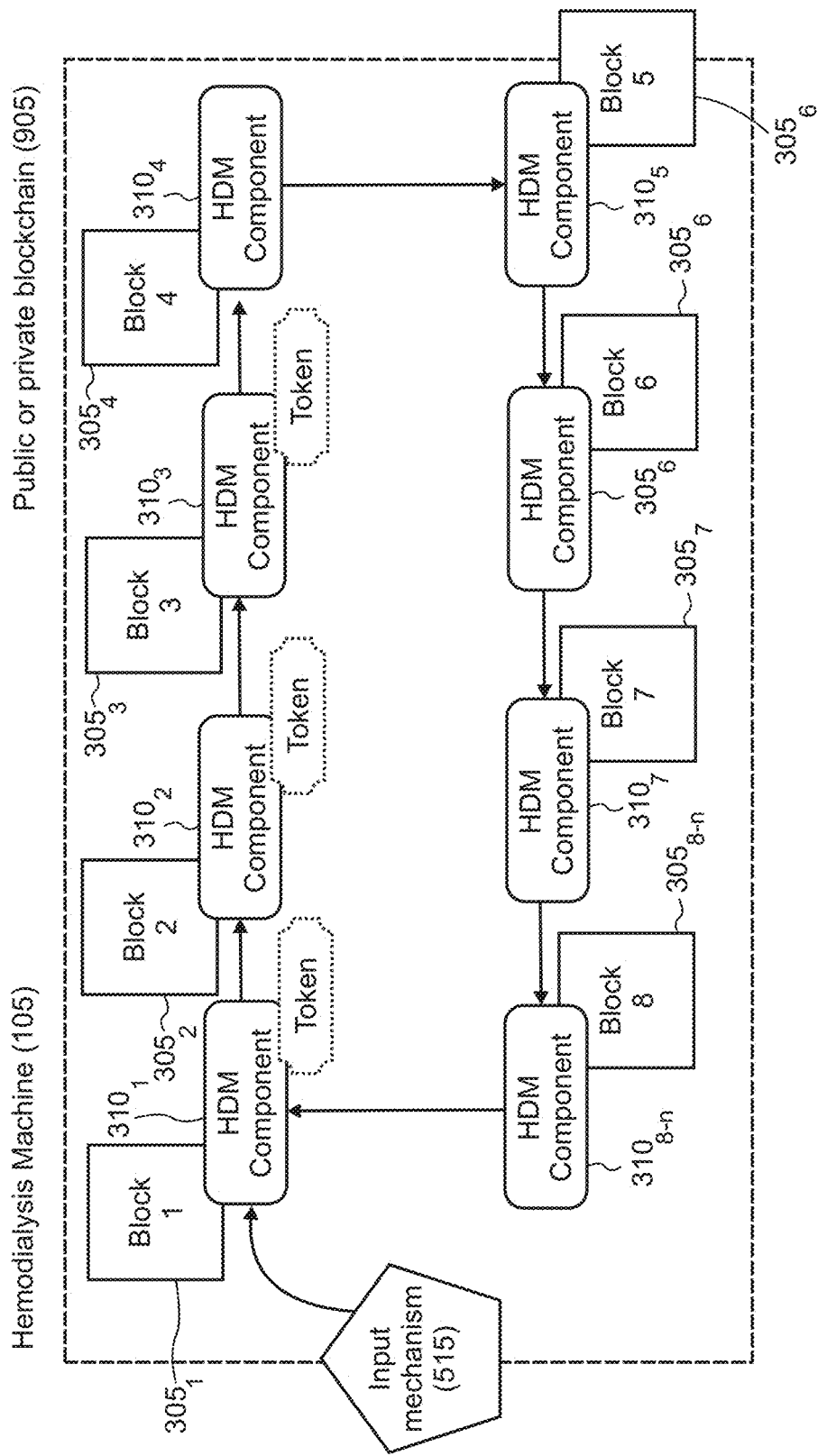
FIG. 9 shows an illustrative representation of sequential blocks in the blockchain created by the hemodialysis machine components.

FIG. 9 shows an illustrative representation in which a token 910 is generated and passed from each hemodialysis machine component 310. The token indicates to the associated SoC for that component to generate a block 305 on the blockchain. The blockchain may be a public or private blockchain, as representatively illustrated by numeral 905. Each SoC may process another block in the blockchain responsive to receiving the token, and each subsequently generated block builds the blockchain.

The token 910 may come equipped with various information, rules, and regulations for how the respective SoC's associated dialysis component 310 can operate. For example, the token may come with an instruction from the remote service 110 (not shown in FIG. 9) for component modifications. Each SoC can verify this instruction each time it receives the token, and a given instruction cannot be executed by a component until the pre-set percentage of components verified the component (e.g., 50%, 90%, etc.). Furthermore, a component is authorized to execute an instruction when that specific component holds the token. Other components may be prevented from executing an instruction if it does not possess the token. Alternatively, a component may have a pre-set period of time (e.g., 10 seconds, two minutes, 10 minutes etc.) to execute an instruction after receiving the token. The set time period may further evade attacks from malicious actors attempting to compromise a component.

Figure 10:
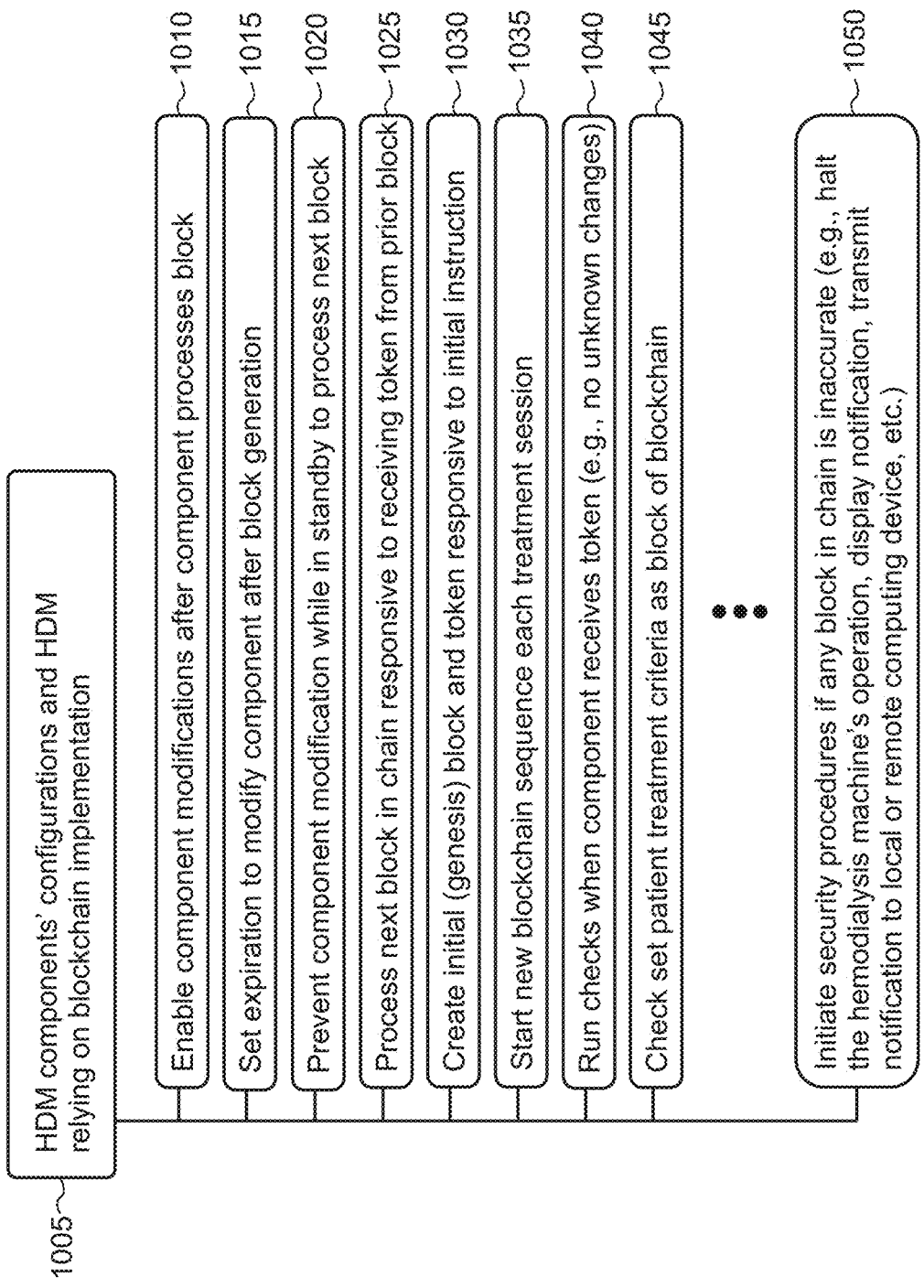
FIG. 10 shows an illustrative schema of configurations of hemodialysis machine components.

FIG. 10 shows an illustrative schema of configurations for hemodialysis machine configurations leveraging a blockchain implementation 1005. The listed configurations are non-exhaustive and may be implemented on a token-based implementation (FIG. 9), non-token-based implementations (FIGS. 5-8), or a hybrid thereof. For example, the implementation shown in FIGS. 5-8 may also utilize a token when checking with the remote service 110.

Exemplary configurations for components include: enable component modifications after a hemodialysis machine component processes block 1010; set expiration to modify component after block generation 1015; prevent component modification while in standby to process next block 1020; process next block in chain responsive to receiving a token from prior block 1025; create initial (genesis) block and token responsive to initial instruction 1030; start new blockchain sequence each treatment session 1035; run checks when a component receives token (e.g., no unknown changes) 1040; check set patient treatment criteria as a block of blockchain 1045; and initiate security procedures if any block in the chain is inaccurate (e.g., halt the hemodialysis machine's operation, display notification, transmit a notification to local or remote computing device, etc.) 1050.

Figure 11:
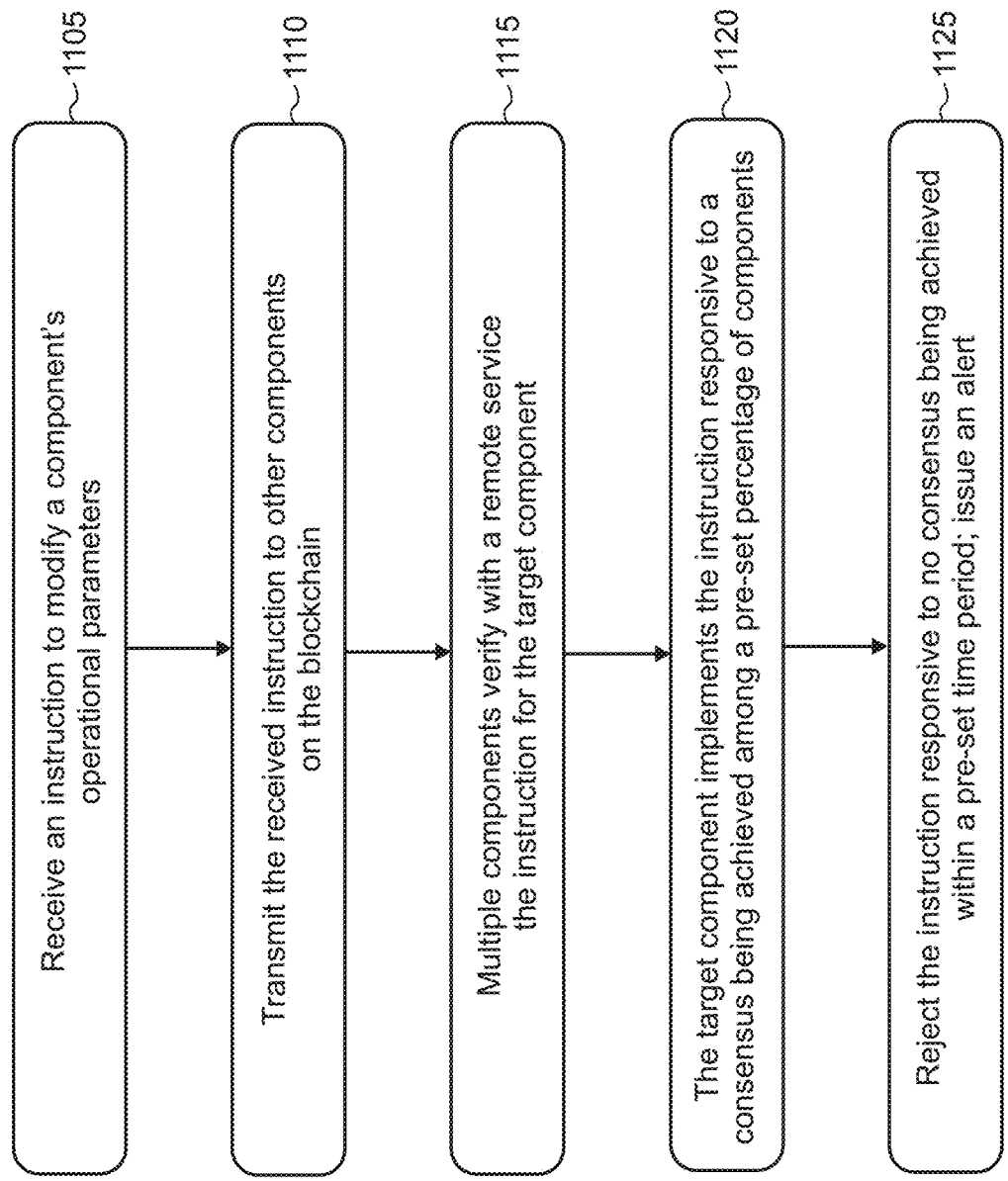
FIG. 11 shows an illustrative flowchart implemented by a hemodialysis machine component.

FIG. 11 shows an illustrative flowchart 1100 of a process implemented by an SoC or processor associated with a hemodialysis machine component 310. In step 1105, the dialysis machine component receives an instruction to modify a component's operational parameters. In step 1110, the SoC transmits the received instruction (or block containing the instruction) to other components operating on the blockchain and utilizes the blockchain application. In step 1115, multiple components verify with a remote service the instruction for the target component. In step 1120, the target component implements the instruction responsive to a consensus among a pre-set percentage of components, and the target component receiving notice of the consensus. In step 1125, the component rejects the instruction responsive to no consensus being achieved within a pre-set time period and may issue an alert. The alert may be, for example, on the dialysis machine itself (e.g., a user interface), a local or remote computing device connected to the dialysis machine, etc.

Figure 12A:
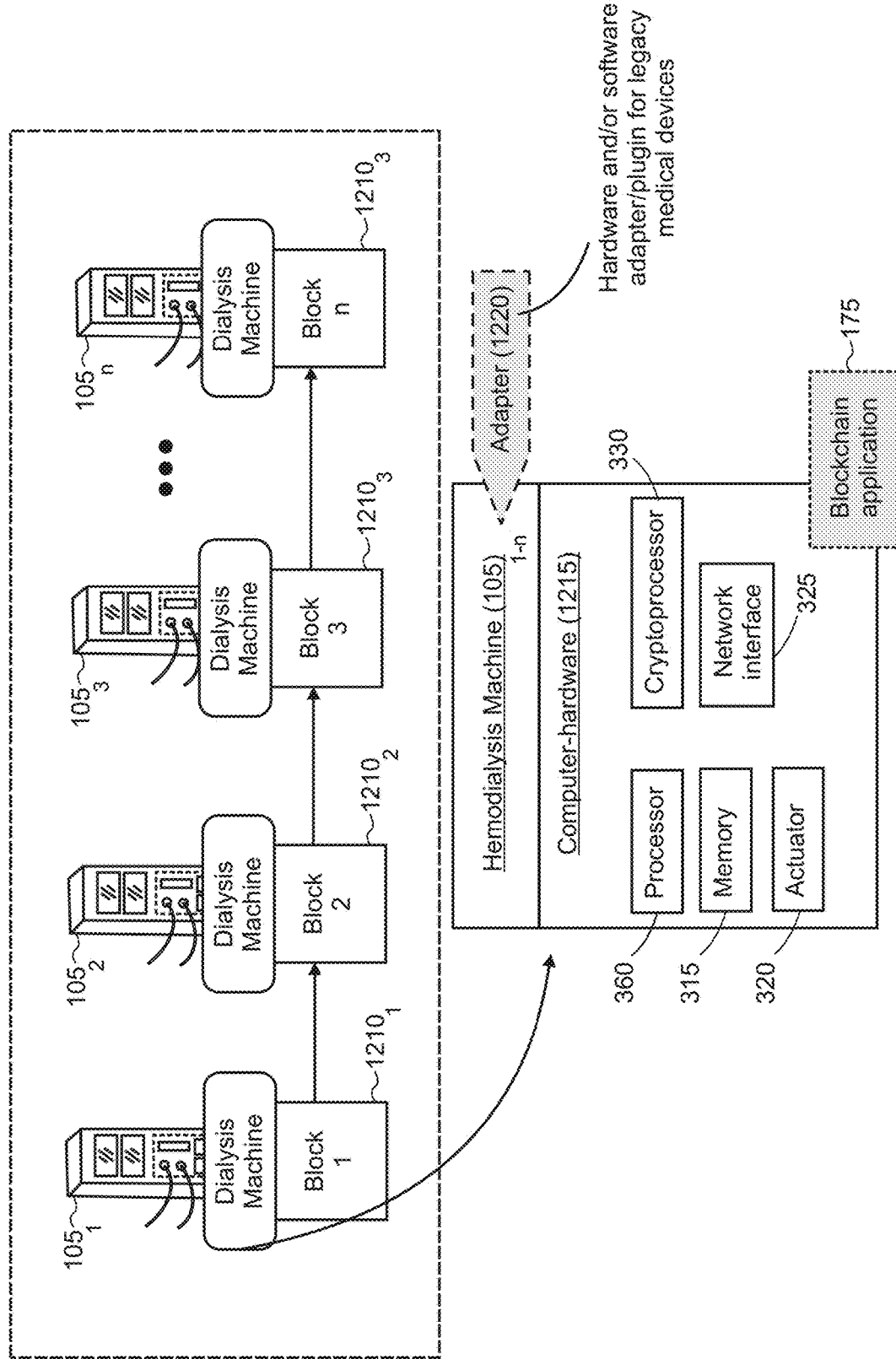
FIG. 12A shows an illustrative blockchain implementation across multiple distinct hemodialysis machines being operated by distinct patients.

FIG. 12A shows an illustrative environment in which the blockchain implementation operates at the medical device level instead of at the component level. The blockchain is formed of blocks 1210 generated by individual dialysis machines 105 that receive operational instruction, such as from a remote service 110. The blockchain implementation may operate in public or private blockchain 1205. The internal computer hardware 1215 for the hemodialysis machines may be similar to that described above with respect to FIGS. 1 and 3 and include a processor 360, memory 315, actuator 320, network interface 325, and cryptoprocessor 330. The dialysis machine 105 may have multiple processors, such as on SoCs as described above, or one or more processors operating the machine's components.

Figure 15:
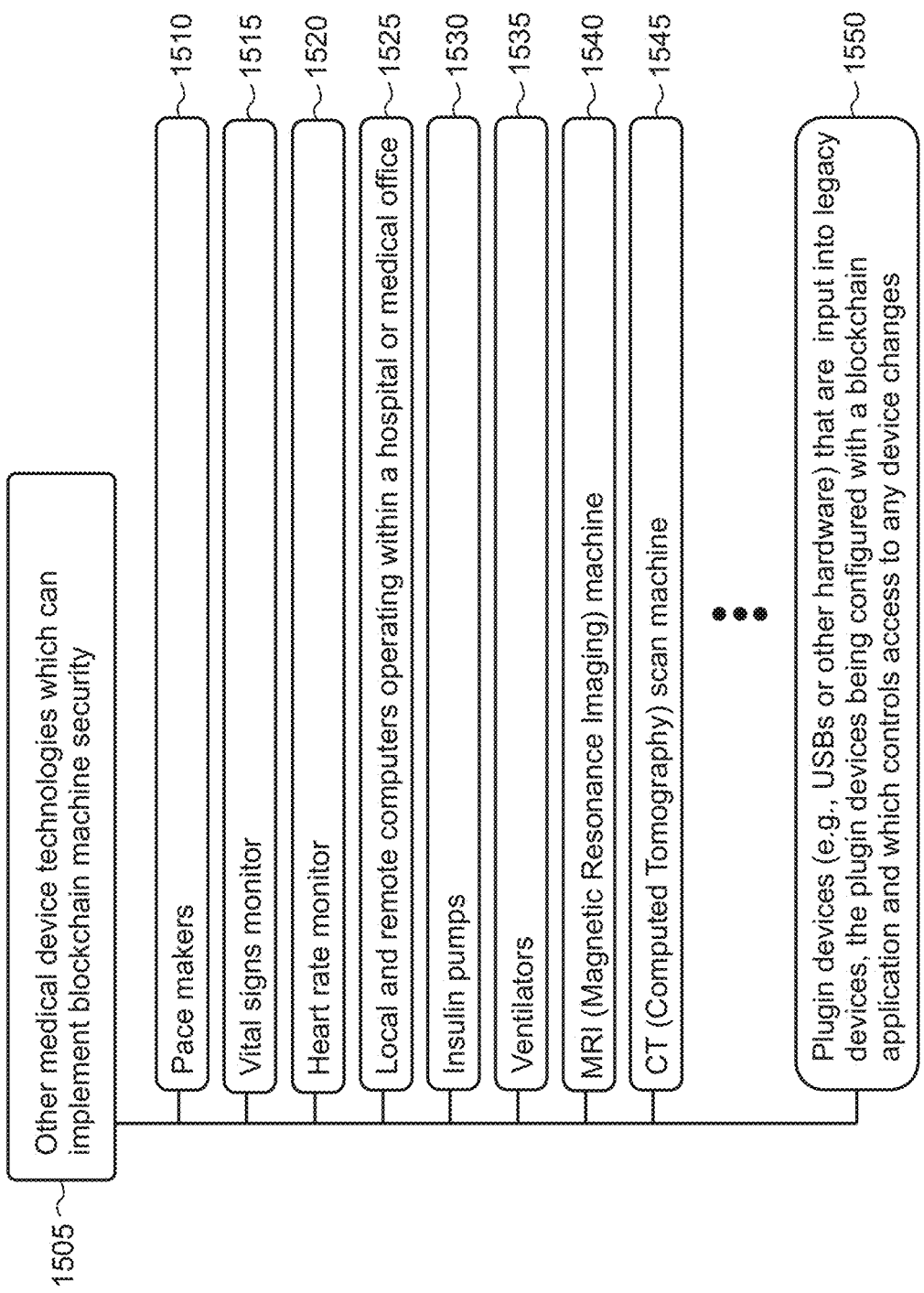
FIG. 15 shows an illustrative schema of other medical device technologies that that present blockchain security protocols can be implemented.

While the implementation shows a hemodialysis machine 105, other medical devices are also possible, such as peritoneal dialysis machines, ventilators, pacemakers, among other medical devices (FIG. 15). Alternatively to the dialysis machine or other medical device specifically configured with the blockchain application, an adapter 1220 may be plugged into the dialysis machine and operate the blockchain application 175 as a separate module.

The adapter 1220 may be a hardware device, such as a separate hardware component configured with the blockchain application 175. The adapter's hardware component may be as simple as a universal serial bus (USB) or sized to accommodate the hardware necessary to implement the features discussed herein, such as to hold memory, processors, a network interface, ports, etc. The hardware adapter may plug into a USB port on the medical device (e.g., USB, micro-USB, macro-USB) or other port. Alternatively, the adapter may be a plugin software application downloaded at the hemodialysis machine or other medical device. This way, for legacy devices or other devices that may make it difficult to download a blockchain application, the adapter can be a cost-effective and easy way to implement the blockchain application and transition the device into the newer world.

Figure 12B:
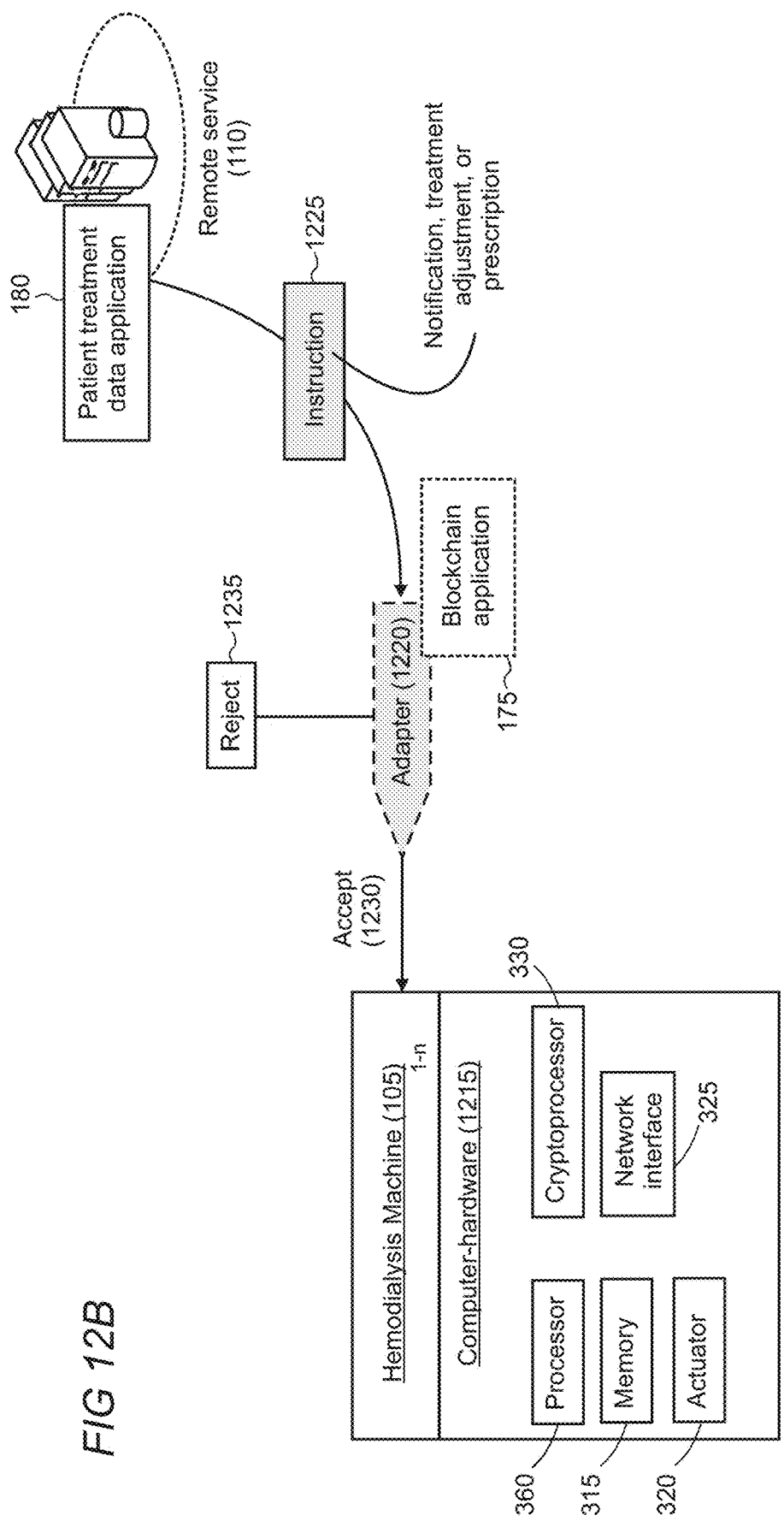
FIG. 12B shows an illustrative environment in which the adapter rejects or accepts a received instruction from the remote service.

FIG. 12B shows an illustrative environment in which an instruction 1225 is transmitted from the remote service 110 to the adapter 1220 connected to the hemodialysis machine 105. The instruction may be a notification prompt that displays on the machine (e.g., "the treatment is almost over," "start treatment soon," "continue treatment longer," etc.), a treatment or prescription instruction, a component modification, etc. The treatment, prescription, or component modification may cause an adjustment to the hemodialysis machine, such as pump speed, the composition of dialysate, starting and ending treatment sessions, etc.

The instruction 1225 from the remote service 110 may derive from the patient treatment data application 180 or some other application that enables providers (e.g., doctors, nurses, technicians, etc.) to create or alter a patient's treatment plan and which is ultimately transmitted to the patient's medical device or associated computing device. Thus, for example, a provider may alter or create a patient's treatment plan on a local computing device (e.g., laptop, PC, smartphone, tablet, etc.) in which the treatment plan is transmitted to the remote service. The remote service may transmit the plan to the respective medical device, such as hemodialysis machine 105. Alternatively, any changes on the provider's computer may be automatically transmitted to the patient and the remote service. In this scenario, the other dialysis machines' ability to check the treatment plan's instruction with the remote service can enhance trust and security over the system's veracity.

The adapter 1220 may be set up with the remote service 110 and the blockchain so that the specific adapter is associated with the hemodialysis machine 105. The adapter functions to act as a stand-between the dialysis machine and the remote service's instructions. The adapter applies the blockchain security to the dialysis machine and then accepts 1230 and passes the instruction onto the dialysis machine or rejects 1235 and suppresses the instruction from advancing to the machine. To enhance its security, the adapter may be configured with tamper-resistant hardware (e.g., a trusted platform module or cryptoprocessor).

Figure 13:
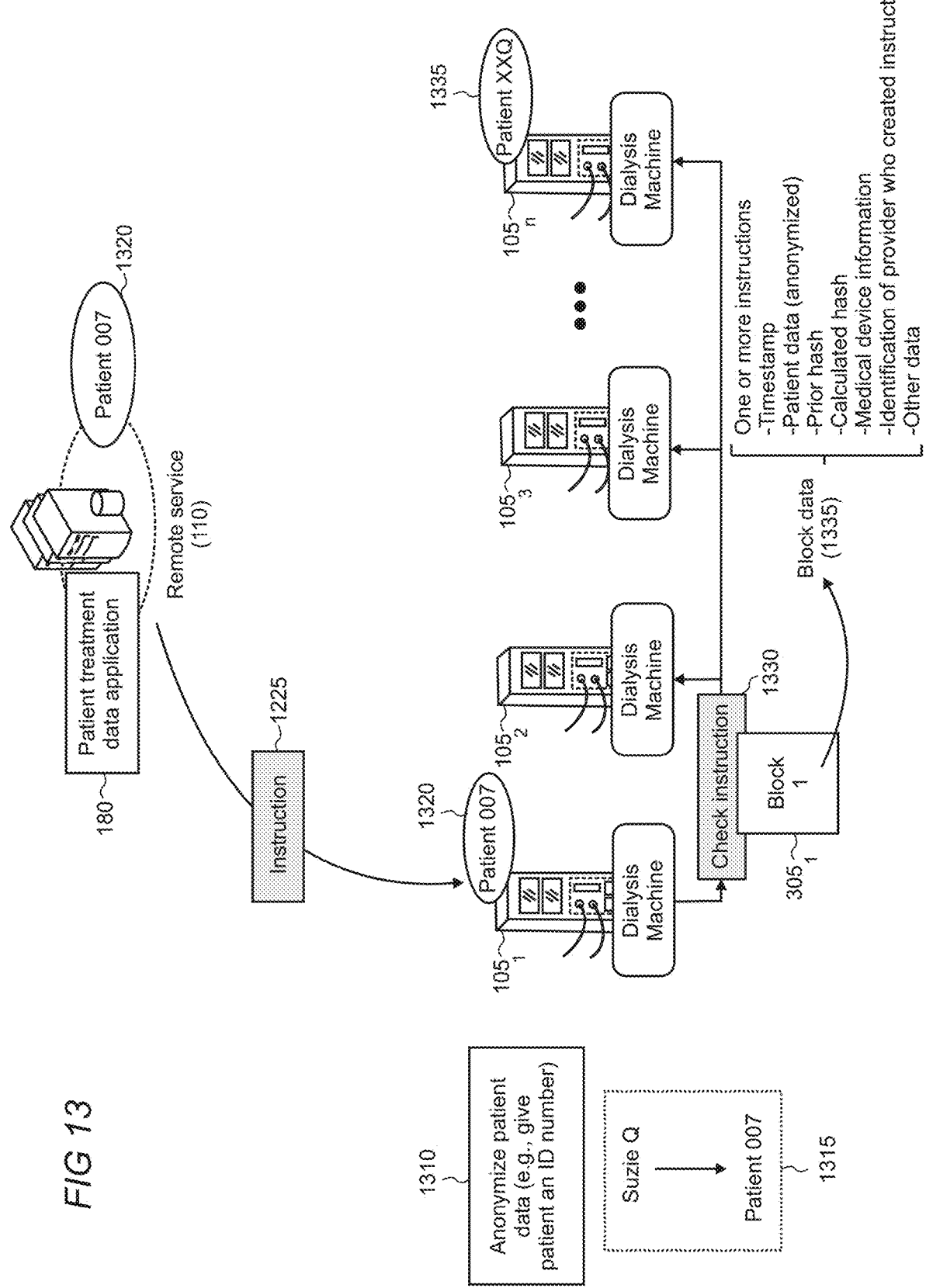
FIG. 13 shows an illustrative instruction being transmitted from a subject hemodialysis machine to other machine's operating the blockchain application.

FIG. 13 shows an illustrative representation in which the hemodialysis machine $105_1$ receives a notification, treatment adjustment, or prescription (such as for a new patient), as representatively shown by numeral 1305. Furthermore, the patient information and data may be anonymized at the remote service 110 and in any instructions, as representatively shown by numeral 1310. For example, each patient may be given an ID number that only the patient and any person or device relevant can know (e.g., the doctor, the remote service, etc.). For example, the patient associated with machine $105_1$, "Suzie Q," may be anonymized to "Patient 007" 1320, as representatively illustrated by numeral 1315. And the patient operating dialysis machine 1055 has been anonymized as "Patient XXQ" 1335.

Upon receiving the instruction 1225 from the remote service 110, the target dialysis machine $105_1$ may then transmit the instruction for checking to other dialysis machines 105 operating the blockchain application 175 to establish a consensus, as representatively illustrated by numeral 1330. The instruction may be formed in a created block $305_1$ that includes various parameters, including the treatment instruction, a notification to the user, a component modification, etc. Exemplary and non-exhaustive block data 1335 can include the one or more instructions, timestamp of the received and/or created instruction, patient data (anonymized in some scenarios), prior hash (if available), calculated hash, medical device information (e.g., type of medical device, serial or manufacturers number for the device, model number of the device, etc.), identification of the signing medical provider who created instruction, and other data. The treatment instruction can include a single component modification or an entire prescription for that patient. Alternatively, the instruction may be a notification that describes the prescription to the patient, and explains to them what manual operations to adjust, such as to switch dialysate or water.

As discussed above with respect to FIG. 1, the instruction may be received by the blockchain application 175 instantiated on the hemodialysis machine 105 (or an associated adapter (FIGS. 12A-B)). Likewise, the remote service's 110 patient treatment data application 180 may interoperate with a blockchain application, either as operating within the same application or leveraging an API to cross-reference each other's features. The hemodialysis machine's blockchain application may process the received instruction through its own sequences before authorizing or rejecting the instruction, such as creating and transmitting the instructional block to other devices on the blockchain network for validation.

Figure 14:
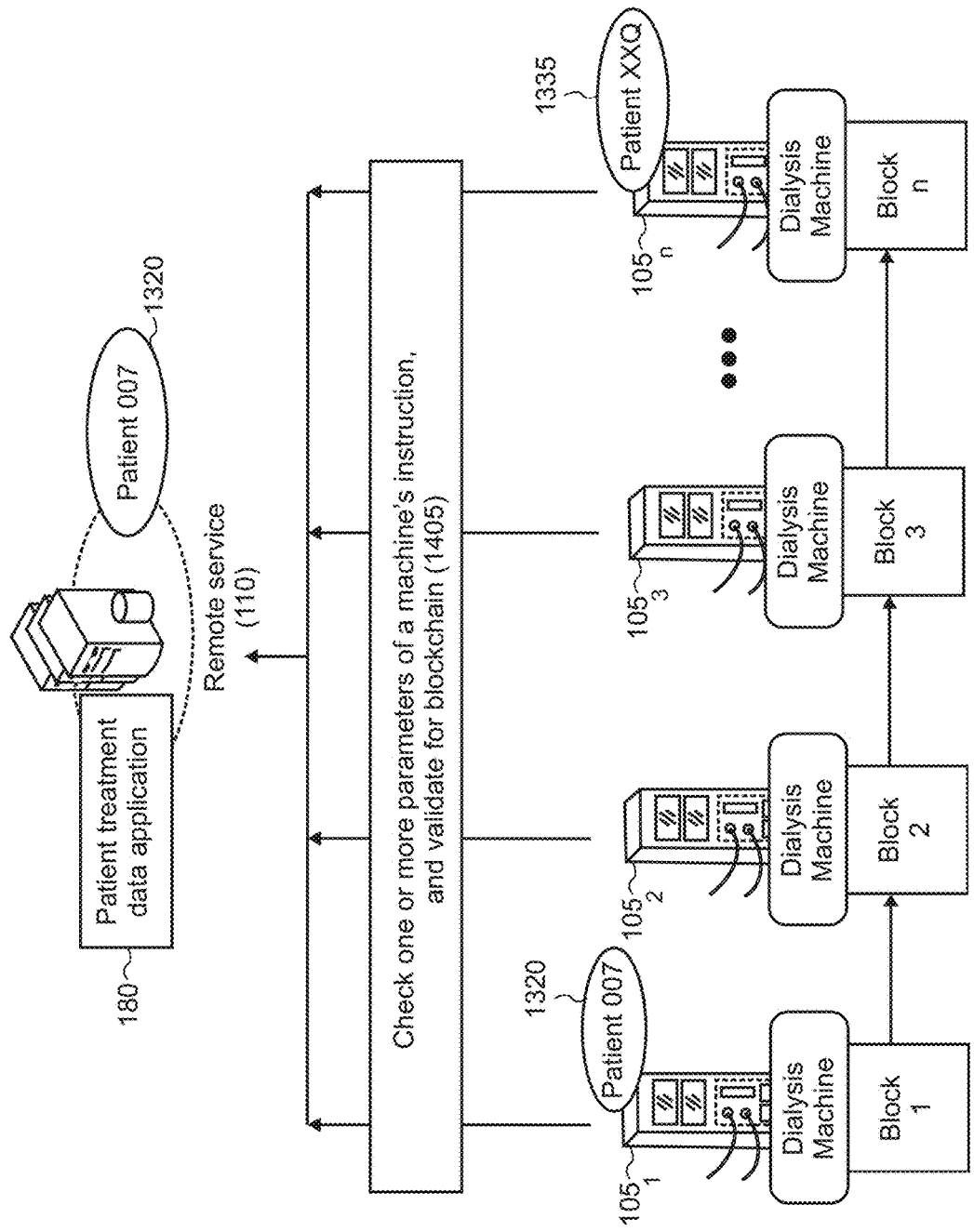
FIG. 14 shows each hemodialysis machine checking the remote service for the instruction.

FIG. 14 shows an illustrative environment in which each dialysis machine 105 that received the instruction 1225 checks the one or more parameters in the instruction with the remote service 110 to validate the instruction for the blockchain, as representatively shown by numeral 1405. Additional dialysis machines and medical devices may check with the remote service, and only an exemplary number is shown in FIG. 14. The dialysis machines may check that the information in the instruction received from the target machine is accurate. For example, the instruction may have included the patient's anonymized ID number, the prescription, treatment adjustment or notification, identifiable information for the specific dialysis machine or medical device (e.g., a serial number for the machine), and other block data 1335 (FIG. 13). The dialysis machines may check the information in the instruction is accurate. The target dialysis machine may locally permit the modification, machine adjustment, or prescription when the instruction has been verified by a pre-set number of machines (e.g., 50%, 90%, etc.). Once the consensus is formed, the created block is added to the blockchain by the medical devices running the blockchain application 175.

As medical devices and dialysis machines 105 may be switched on and off periodically, the blockchain application 175 may be configured to update accordingly. Machines that have been off can be updated on the blockchain updates. Furthermore, different genres of medical devices can utilize the blockchain application security features. For example, a dialysis machine instruction can be transmitted to other types of medical devices, like a vital signs monitor, insulin pumps, ventilators, etc. This may help increase the number of devices operating the blockchain application. Since distinct medical devices can come with distinct security software, this can heighten the security of the blockchain.

FIG. 14 likewise shows that other hemodialysis machines 105 operating on the blockchain 305 create blocks. Thus, blocks 1, 2, 3, and n (for any number of blocks) can be tied together to create the immutable blockchain structure. Each block may have been created similarly to Block 1 discussed above, that is, each block is a specific instruction received from a remote service 110 that has been validated according to a consensus of other dialysis machines 105.

FIG. 15 shows an illustrative schema of other medical device technologies which can implement blockchain machine security 1505. Exemplary and non-exhaustive medical device technologies can include pacemakers 1510, vital signs monitor 1515, heart rate monitor 1520, local and remote computers operating within a hospital or medical office 1525, insulin pumps 1530, ventilators 1535, MRI (Magnetic Resonance Imaging) machines 1540, CT (Computer Tomography) scan machines 1545, and plugin devices (e.g., USBs (Universal Serial Buses) or other hardware) that are input into legacy devices, the plugin devices being configured with a blockchain application and which controls access to any device changes.

In some scenarios, multiple types of medical devices can operate on the same blockchain and thereby regulate each other. For example, insulin pumps, ventilators, and dialysis machines can all validate each other's instructions on the same blockchain network. The permissioned public or private blockchain among these medical devices may depend on their specific configurations, security parameters, or manufacturers, among other traits.

In other scenarios and as an exemplary implementation of another medical device, the current blockchain security implementation may work with a ventilator. For example, respective SoCs may be tied to a ventilator's sensors, expiratory valve, fresh gas source, humidifier, and inspiratory valve. As discussed above, an operational instruction may be transmitted to one or more of these components, which can be verified by other distinct components operating within the medical device. Validation by other components can result in approval and execution of the instruction. The token embodiment discussed above with respect to FIGS. 9 and 10 is also possible. Likewise, the higher level ventilator-level implementation is also possible, in which multiple ventilators approve each other's instructions on a blockchain. The same concept is implementable among virtually all medical devices, as non-exhaustively and exemplarily shown in FIG. 15.

Figure 16:
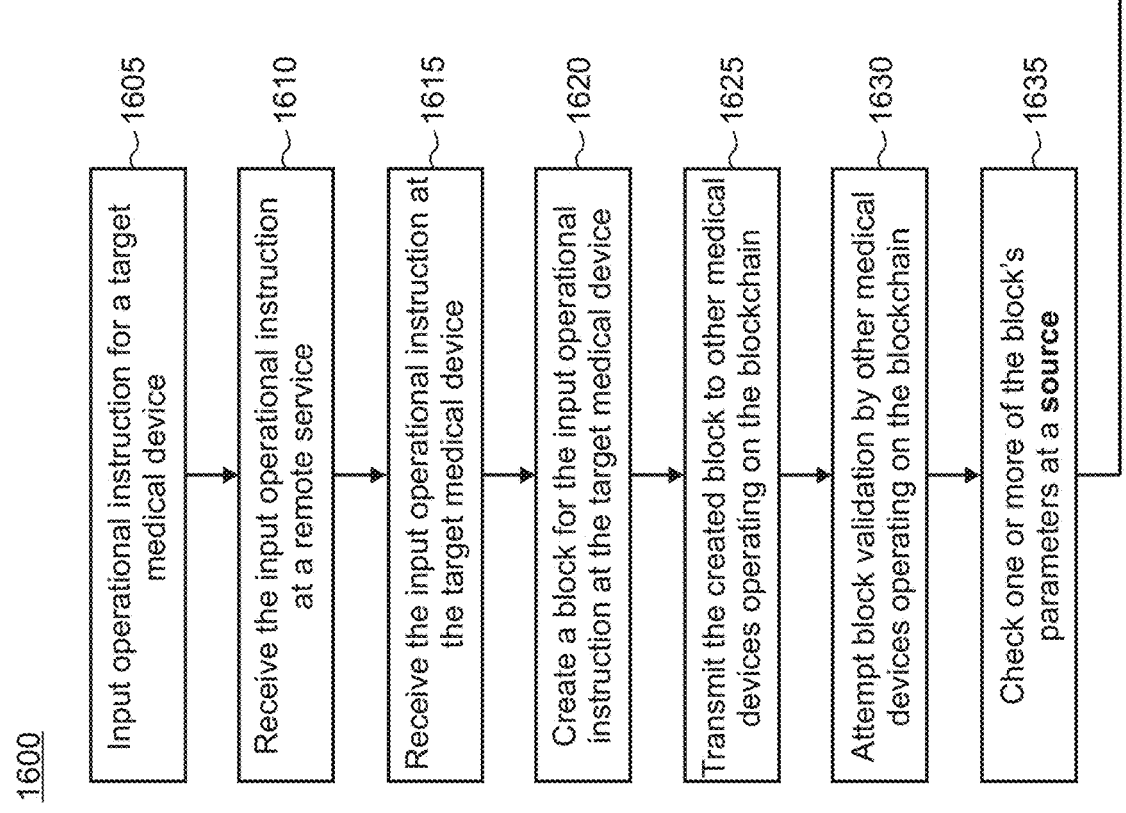
FIGS. 16-18 show illustrative flowcharts of processes that may be implemented by a medical device, such as the hemodialysis machine, implementing the present blockchain security protocols.

FIG. 16 shows a flowchart of a method 1600, which may be performed by a medical device (e.g., dialysis machine) or associated computing device. In step 1605, an operational instruction for a target medical device is input into a computing device. The computing device may be associated with a medical provider that manages a patient's illness. In step 1610, the input operational instruction is received at a remote service. The remote service may store various patient data and electronic medical records (EMRs) as a cloud storage provider for backup and easier access. In step 1615, the target medical device receives the input operational instruction by the medical provider. The instruction may have been received from the remote service or directly from the medical provider's input device.

In step 1620, the target medical device or associated computing device creates a block for the input operational instruction. The block can contain various data, including instruction data, patient data (which may be anonymized), timestamps, the medical provider's identification (e.g., name or license number), etc. In step 1625, the target medical device transmits the created block to other medical devices operating on the blockchain. Alternatively, the target medical device may send the instruction not tied to any specific block. In step 1630, the other distinct medical devices operating on the blockchain may attempt validation of the block received from the target medical device.

In step 1635, the other medical devices check one or more of the block's parameters from a source. In typical implementations, the checking may be done at the remote service that holds various patient information, but the present implementation is not limited thereto. Any computing device or storage location may be checked to validate the operational instruction, including a hospital or medical office's computer system, the patient's own computing device or machine that stores that intended instruction, etc.

In step 1640, the medical devices establish a consensus for the block based on sufficient validation of the operational instruction. Consensus may be achieved based on some pre-set number of validations of the instruction within the specific blockchain application, such as 50%, 75%, 90%, or 100%. In step 1645, the target medical device executes the operational instruction after consensus has been reached. The target medical device may wait to execute the instruction to ensure that the instruction is not some corrupt instruction from a malicious hacker or otherwise bad actor. Furthermore, such instructions can create accountability to medical providers by creating an immutable ledger of any and all changes to a patient's medical record.

Alternatively, if consensus cannot be reached among the medical devices, the target medical device may issue a prompt or warning about the failed system update and implement other security measures. Other medical devices on the blockchain network may likewise implement security measures, or other devices may continue to operate the blockchain application until a pre-set number of failures occur, such as two, three, etc. As inaccuracies can happen from time to time (such as a syncing problem, the medical provider quickly corrected a mistake, etc.), the blockchain application may not be compromised after a single failure.

Figure 17:
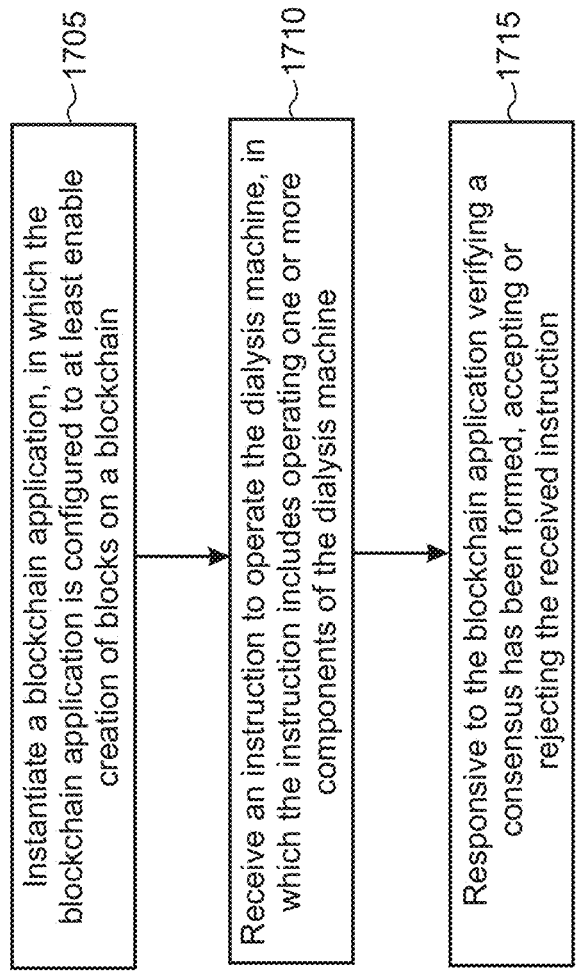

In step 1705, in FIG. 17, a dialysis machine may instantiate a blockchain application, in which the blockchain application is configured to at least enable the creation of blocks on a blockchain. In step 1710, the dialysis machine receives an instruction to operate the machine, in which the instruction includes operating one or more components of the dialysis machine. In step 1715, responsive to the blockchain application verifying a consensus has been formed, accepting or rejecting the received instruction.

Figure 18:
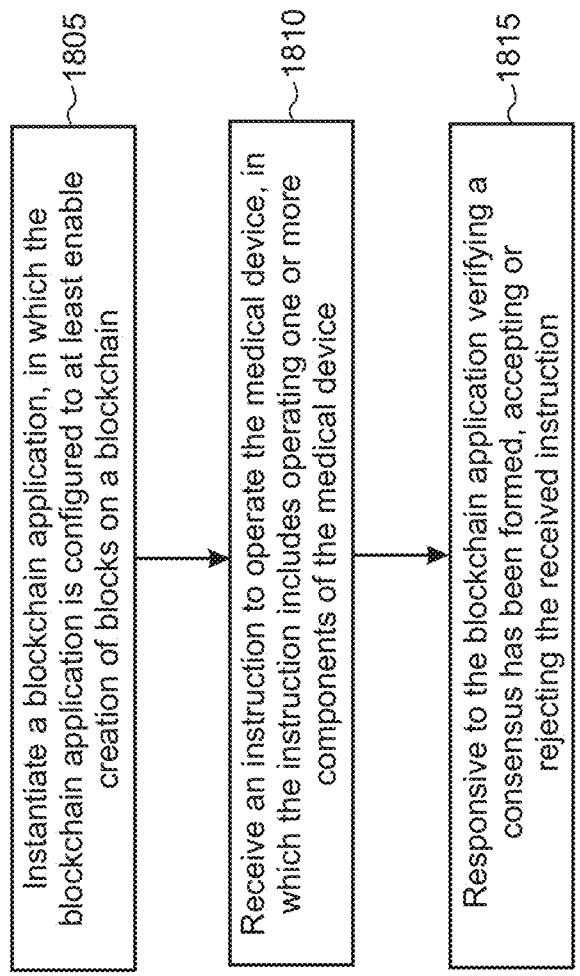

In step 1805, in FIG. 18, a medical device may instantiate a blockchain application, in which the blockchain application is configured to at least enable the creation of blocks on a blockchain. In step 1810, the medical device receives an instruction to operate the device, in which the instruction includes operating one or more components of the medical device. In step 1815, responsive to the blockchain application verifying a consensus has been formed, accepting or rejecting the received instruction.

Figure 19:
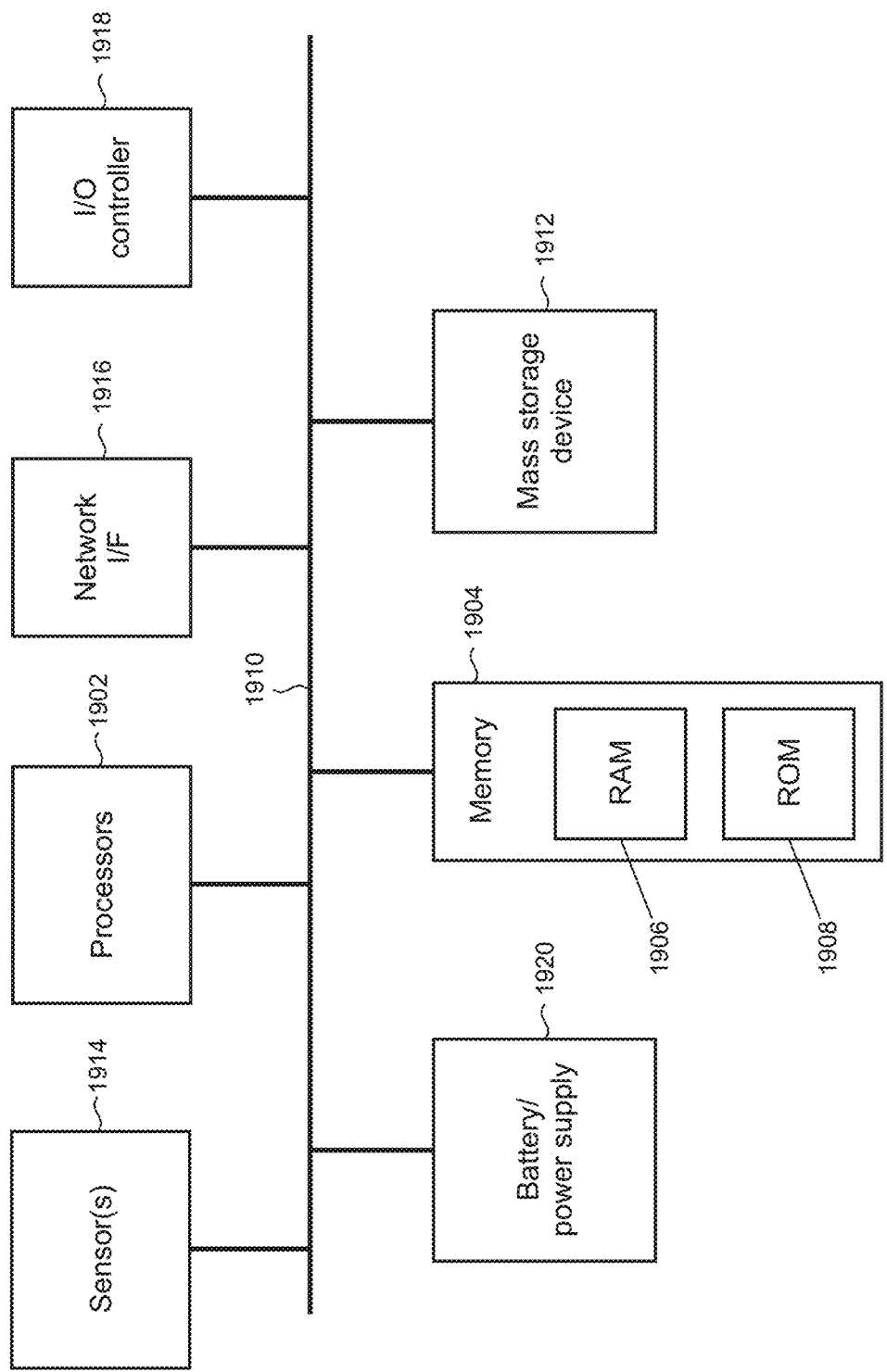
FIG. 19 is a simplified block diagram of an illustrative architecture of a computing device or medical device that may be used at least in part to implement the present leveraging blockchain to secure dialysis machine components.

FIG. 19 shows an illustrative architecture 1900 for a computing device such as a laptop computer, personal computer, a hemodialysis machine, or other medical devices for the present leveraging blockchain to secure dialysis components and maintain operational logs. The architecture 1900 may be non-exhaustive for a given computing device (namely, medical devices) but may be utilized to execute the functions described herein. Thus, for example, the architecture may be used in addition to the functions of the dialysis machine's components depicted in FIG. 2.

The architecture 1900 illustrated in FIG. 19 includes one or more processors 1902 (e.g., central processing unit, dedicated Artificial Intelligence chip, graphics processing unit, etc.), a system memory 1904, including RAM (random access memory) 1906 and ROM (read-only memory) 1908, and a system bus 1910 that operatively and functionally couples the components in the architecture 1900. A basic input/output system containing the basic routines that help to transfer information between elements within the architecture 1900, such as during startup, is typically stored in the ROM 1908. The architecture 1900 further includes a mass storage device 1912 for storing software code or other computer-executed code that is utilized to implement applications, the file system, and the operating system. The mass storage device 1912 is connected to the processor 1902 through a mass storage controller (not shown) connected to the bus 1910. The mass storage device 1912 and its associated computer-readable storage media provide non-volatile storage for the architecture 1900. Although the description of computer-readable storage media contained herein refers to a mass storage device, such as a hard disk or CD-ROM drive, it may be appreciated by those skilled in the art that computer-readable storage media can be any available storage media that can be accessed by the architecture 1900.

By way of example, and not limitation, computer-readable storage media may include volatile and non-volatile, removable and non-removable media implemented in any method or technology for storage of information such as computer-readable instructions, data structures, program modules, or other data. For example, computer-readable media includes, but is not limited to, RAM, ROM, EPROM (erasable programmable read-only memory), EEPROM (electrically erasable programmable read-only memory), Flash memory or other solid-state memory technology, CD-ROM, DVD, HD-DVD (High Definition DVD), Blu-ray, or other optical storage, a magnetic cassette, magnetic tape, magnetic disk storage or other magnetic storage device, or any other medium which can be used to store the desired information and which can be accessed by the architecture 1900.

According to various embodiments, the architecture 1900 may operate in a networked environment using logical connections to remote computers through a network. The architecture 1900 may connect to the network through a network interface unit 1916 connected to the bus 1910. It may be appreciated that the network interface unit 1916 also may be utilized to connect to other types of networks and remote computer systems. The architecture 1900 also may include an input/output controller 1918 for receiving and processing input from a number of other devices, including a keyboard, mouse, touchpad, touchscreen, control devices such as buttons and switches, or electronic stylus (not shown in FIG. 19). Similarly, the input/output controller 1918 may provide output to a display screen, user interface, a printer, or other output device types (also not shown in FIG. 19).

It may be appreciated that the software components described herein may, when loaded into the processor 1902 and executed, transform the processor 1902 and the overall architecture 1900 from a general-purpose computing system into a special-purpose computing system customized to facilitate the functionality presented herein. The processor 1902 may be constructed from any number of transistors or other discrete circuit elements, which may individually or collectively assume any number of states. More specifically, the processor 1902 may operate as a finite-state machine in response to executable instructions contained within the software modules disclosed herein. These computer-executable instructions may transform the processor 1902 by specifying how the processor 1902 transitions between states, thereby transforming the transistors or other discrete hardware elements constituting the processor 1902.

Encoding the software modules presented herein also may transform the physical structure of the computer-readable storage media presented herein. The specific transformation of physical structure may depend on various factors in different implementations of this description. Examples of such factors may include but are not limited to, the technology used to implement the computer-readable storage media, whether the computer-readable storage media is characterized as primary or secondary storage, and the like. For example, if the computer-readable storage media is implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media when the software is encoded therein. These transformations may include altering the magnetic characteristics of particular locations within given magnetic media. These transformations also may include altering the physical features or characteristics of particular locations within given optical media to change the optical characteristics of those locations. Other transformations of physical media are possible without departing from the scope and spirit of the present description, with the foregoing examples provided only to facilitate this discussion.

The architecture 1900 may further include one or more sensors 1914 or a battery or power supply 1920. The sensors may be coupled to the architecture to pick up data about an environment or a component, including temperature, pressure, etc. Exemplary sensors can include a thermometer, accelerometer, smoke or gas sensor, pressure sensor (barometric or physical), light sensor, ultrasonic sensor, gyroscope, among others. The power supply may be adapted with an AC power cord or a battery, such as a rechargeable battery for portability.

In light of the above, it may be appreciated that many types of physical transformations take place in the architecture 1900 in order to store and execute the software components presented herein. It also may be appreciated that the architecture 1900 may include other types of computing devices, including wearable devices, handheld computers, embedded computer systems, smartphones, PDAs, and other types of computing devices known to those skilled in the art. It is also contemplated that the architecture 1900 may not include all of the components shown in FIG. 19, may include other components that are not explicitly shown in FIG. 19, or may utilize an architecture completely different from that shown in FIG. 19.

FIG. 20 is a simplified block diagram of an illustrative computer system 2000 such as a PC or server (such as remote service 110) with which the present leveraging blockchain to secure dialysis components and maintain operational logs may be implemented. The computer system may likewise be utilized by a medical device, such as a hemodialysis machine, pacemaker, vital signs monitor, etc., to effectuate the functions described herein.

Computer system 2000 includes a processor 2005, a system memory 2011, and a system bus 2014 that couples various system components including the system memory 2011 to the processor 2005. The system bus 2014 may be any of several types of bus structures, including a memory bus or memory controller, a peripheral bus, or a local bus using any of a variety of bus architectures. The system memory 2011 includes read-only memory (ROM) 2017 and random-access memory (RAM) 2021. A basic input/output system (BIOS) 2025, containing the basic routines that help to transfer information between elements within the computer system 2000, such as during startup, is stored in ROM 2017. The computer system 2000 may further include a hard disk drive 2028 for reading from and writing to an internally disposed hard disk (not shown), a magnetic disk drive 2030 for reading from, or writing to a removable magnetic disk 2033 (e.g., a floppy disk), and an optical disk drive 2038 for reading from or writing to a removable optical disk 2043 such as a CD (compact disc), DVD (digital versatile disc), or other optical media. The hard disk drive 2028, magnetic disk drive 2030, and optical disk drive 2038 are connected to the system bus 2014 by a hard disk drive interface 2046, a magnetic disk drive interface 2049, and an optical drive interface 2052, respectively. The drives and their associated computer-readable storage media provide non-volatile storage of computer-readable instructions, data structures, program modules, and other data for the computer system 2000.

Although this illustrative example includes a hard disk, a removable magnetic disk 2033, and a removable optical disk 2043, other types of computer-readable storage media which can store data that is accessible by a computer such as magnetic cassettes, Flash memory cards, digital video disks, data cartridges, random access memories (RAMs), read-only memories (ROMs), and the like may also be used in some applications of the present leveraging blockchain to secure dialysis components and maintain operational logs. In addition, as used herein, the term computer-readable storage media includes one or more instances of a media type (e.g., one or more magnetic disks, one or more CDs, etc.). For purposes of this specification and the claims, the phrase "computer-readable storage media" and variations thereof are intended to cover non-transitory embodiments and do not include waves, signals, and/or other transitory and/or intangible communication media.

A number of program modules may be stored on the hard disk, magnetic disk 2033, optical disk 2043, ROM 2017, or RAM 2021, including an operating system 2055, one or more application programs 2057, other program modules 2060, and program data 2063. A user may enter commands and information into the computer system 2000 through input devices such as a keyboard 2066 and pointing device 2068 such as a mouse. Other input devices (not shown) may include a microphone, joystick, gamepad, satellite dish, scanner, trackball, touchpad, touchscreen, touch-sensitive device, voice-command module or device, user motion or user gesture capture device, or the like. These and other input devices are often connected to the processor 2005 through a serial port interface 2071 that is coupled to the system bus 2014 but may be connected by other interfaces, such as a parallel port, game port, or universal serial bus (USB). A monitor 2073 or other type of display device is also connected to the system bus 2014 via an interface, such as a video adapter 2075. In addition to the monitor 2073, personal computers typically include other peripheral output devices (not shown), such as speakers and printers. The illustrative example shown in FIG. 20 also includes a host adapter 2078, a Small Computer System Interface (SCSI) bus 2083, and an external storage device 2076 connected to the SCSI bus 2083.

The computer system 2000 is operable in a networked environment using logical connections to one or more remote computers, such as a remote computer 2088. The remote computer 2088 may be selected as another personal computer, a server, a router, a network PC, a peer device, or other common network node, and typically includes many or all of the elements described above relative to the computer system 2000, although only a single representative remote memory/storage device 2090 is shown in FIG. 20. The logical connections depicted in FIG. 20 include a local area network (LAN) 2093 and a wide area network (WAN) 2095. Such networking environments are often deployed, for example, in offices, enterprise-wide computer networks, intranets, and the Internet.

When used in a LAN networking environment, the computer system 2000 is connected to the local area network 2093 through a network interface or adapter 2096. When used in a WAN networking environment, the computer system 2000 typically includes a broadband modem 2098, network gateway, or other means for establishing communications over the wide area network 2095, such as the Internet. The broadband modem 2098, which may be internal or external, is connected to the system bus 2014 via a serial port interface 2071. In a networked environment, program modules related to the computer system 2000, or portions thereof, may be stored in the remote memory storage device 2090. It is noted that the network connections shown in FIG. 20 are illustrative, and other means of establishing a communications link between the computers may be used depending on the specific requirements of an application of the present leveraging blockchain to secure dialysis components and maintain operational logs.

Various exemplary embodiments are described herein. In one exemplary embodiment, disclosed is a dialysis machine that leverages blockchain to safeguard machine operations, comprising: one or more processors; and one or more hardware-based memory devices storing computer-readable instructions which, when executed by the one or more processors, cause the dialysis machine to: instantiate a blockchain application, in which the blockchain application is configured to at least enable creation of blocks on a blockchain; receive an instruction to operate the dialysis machine, in which the instruction includes operating one or more components of the dialysis machine or modifying one or more operational components of the dialysis machine; and responsive to the blockchain application verifying a consensus has been formed: accepting and executing the received instruction at the dialysis machine; or rejecting the received instruction.

As another example, the executed instructions further cause the dialysis machine to: responsive to receiving the instruction, transmit the instruction to one or more other distinct computing devices, wherein the distinct computing devices verify the instruction; and establish the consensus based on the distinct computing devices verifying the instruction. As another example, the distinct computing devices include any one or more of hemodialysis machines, peritoneal dialysis machines, personal computers, laptop computers, or other medical devices. In another example, the consensus is formed when at least 50% of devices on the blockchain agree on the instruction. As a further example, the distinct computing devices verify the instruction by checking with a remote service that stores the instruction. As a further example, the executed instructions further cause the dialysis machine to create a block for the blockchain based on the received instruction, in which the instruction, within the created block, is transmitted for verification by the distinct computing devices. As a further example, the created block includes information about and surrounding the instruction, including any one or more of who prescribed the instruction, dialysis machine information, and location information for the patient or dialysis machine. In another example, patient information in the instruction and in the created block is anonymized. In another example, the executed instructions further cause the dialysis machine to verify one or more instructions for the distinct computing devices operating on the blockchain, wherein the verifying includes checking the one or more instructions with the remote service, and subsequently forming the consensus for those one or more instructions. In another example, further comprising: an adapter plugged into the dialysis machine, in which the adapter stores the one or more processors, the one or more hardware-based memory devices, and the blockchain application, and wherein the adapter interoperates with the hemodialysis machine's operations, such that the adapter authorizes or suppresses instructions to the hemodialysis machine.

In another exemplary embodiment, disclosed is a method performed by a dialysis machine or an adapter connected to the dialysis machine, comprising: instantiating, using one or more processors associated with the dialysis machine, a blockchain application, in which the blockchain application is configured to enable creation of blocks on a blockchain by the dialysis machine; receive, at the one or more processors, an instruction to operate the dialysis machine, in which the instruction includes operating one or more components of the dialysis machine or modifying one or more operational components of the dialysis machine; and responsive to the blockchain application verifying a consensus has been formed: accepting and executing, by the one or more processors, received instruction at the dialysis machine; or rejecting, by the one or more processors, the received instruction. In another example, further comprising: responsive to receiving the instruction, transmitting the instruction to one or more other distinct computing devices, wherein the distinct computing devices verify the instruction; and receiving the consensus from the distinct computing devices. As another example, the distinct computing devices include any one or more of hemodialysis machines, peritoneal dialysis machines, personal computers, laptop computers, or other medical devices. As another example, the consensus is formed when at least 50% of devices on the blockchain agree on the instruction. In another example, the distinct computing devices verify the instruction by checking with a remote service that stores the instruction. In another example, further comprising creating a block for the blockchain based on the received instruction, in which the instruction, within the created block, is transmitted for verification by the distinct computing devices.

In another exemplary embodiment, disclosed is one or more hardware-based non-transitory computer-readable memory devices disposed in a medical device, the computer-readable instructions, when executed by one or more processors, cause the medical device to: instantiate a blockchain application, in which the blockchain application is configured to enable creation of blocks on a blockchain; receive an instruction to operate the dialysis machine, in which the instruction includes operating one or more components of the dialysis machine or modifying one or more operational components of the dialysis machine; and responsive to the blockchain application verifying a consensus has been formed: accepting and executing received instruction at the dialysis machine; or rejecting the received instruction.

As another example, the medical device is a hemodialysis machine. As another example, the executed instructions further cause the medical device to: responsive to receiving the instruction, transmit the instruction to one or more other distinct medical devices, wherein the distinct medical devices verify the instruction; and receive the consensus from the distinct medical devices. In another example, the patient information in the instruction is anonymized.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A medical device that leverages blockchain to safeguard machine operations, comprising:
   one or more processors; and
   one or more hardware-based memory devices storing computer-readable instructions which, when executed by the one or more processors, cause the medical device to:
      instantiate a blockchain application, in which the blockchain application is configured to at least enable creation of blocks on a blockchain;
      receive an instruction to operate the medical device, in which the instruction includes modifying one or more operational components of the medical device from a previous treatment;
      accept and execute the received instruction to modify the one or more operational components at the medical device responsive to a consensus being formed within a blockchain, wherein executing includes modifying a mechanism at the medical device;
      receive a subsequent instruction to operate the medical device, in which the subsequent instruction included operating one or more components of the medical device or modifying one or more operational components of the medical device; and
      reject the received subsequent instruction at the medical device responsive to the consensus not being formed within the blockchain.

2. The medical device of claim 1, wherein the executed instructions further cause the medical device to:
   responsive to receiving the instruction, transmit the instruction to one or more other distinct computing devices, wherein the distinct computing devices verify the instruction; and
   establish the consensus based on the distinct computing devices verifying the instruction.

3. The medical device of claim 2, wherein the distinct computing devices include any one or more of hemodialysis machines, peritoneal dialysis machines, personal computers, laptop computers, or other medical devices.

4. The medical device of claim 2, wherein the consensus is formed when at least 50% of devices on the blockchain agree on the instruction.

5. The medical device of claim 4, wherein the distinct computing devices verify the instruction by checking with a remote service that stores the instruction.

6. The medical device of claim 5, wherein the executed instructions further cause the medical device to create a block for the blockchain based on the received instruction, in which the instruction, within the created block, is transmitted for verification by the distinct computing devices.

7. The medical device of claim 6, wherein the created block includes information about and surrounding the instruction, including any one or more of who prescribed the instruction, medical device information, and location information for the patient or medical device.

8. The medical device of claim 6, wherein patient information in the instruction and in the created block is anonymized.

9. The medical device of claim 1, wherein the executed instructions further cause the medical device to verify one or more instructions for the distinct computing devices operating on the blockchain, wherein the verifying includes checking the one or more instructions with the remote service, and subsequently forming the consensus for those one or more instructions.

10. The medical device of claim 1, further comprising:
   an adapter plugged into the medical device, in which the adapter stores the one or more processors, the one or more hardware-based memory devices, and the blockchain application, and
   wherein the adapter interoperates with the hemodialysis machine's operations, such that the adapter authorizes or suppresses instructions to the hemodialysis machine.

11. A method performed by a medical device or an adapter connected to the medical device, comprising:
- instantiating, using one or more processors associated with the medical device, a blockchain application, in which the blockchain application is configured to enable creation of blocks on a blockchain by the medical device;
- receiving, at the one or more processors, an instruction to operate the medical device, in which the instruction includes modifying one or more operational components of the medical device from a previous treatment;
- accepting and executing the received instruction to modify the one or more operational components as the medical device responsive to a consensus being formed within a blockchain, wh rein executing includes modifying a mechanism at the medical device;
- receiving a subsequent instruction to operate the medical device, in which the subsequent instruction includes derating one or more components of the medical device or modifying one or more operational components of the medical device, and
- rejecting the received subsequent instruction at the medical device responsive to the consensus not being formed within the blockchain.

12. The method of claim 11, further comprising:
- responsive to receiving the instruction, transmitting the instruction to one or more other distinct computing devices, wherein the distinct computing devices verify the instruction; and
- receiving the consensus from the distinct computing devices.

13. The method of claim 12, wherein the distinct computing devices include any one or more of hemodialysis machines, peritoneal dialysis machines, personal computers, laptop computers, or other medical devices.

14. The method of claim 12, wherein the consensus is formed when at least 50% of devices on the blockchain agree on the instruction.

15. The method of claim 14, wherein the distinct computing devices verify the instruction by checking with a remote service that stores the instruction.

16. The method of claim 15, further comprising creating a block for the blockchain based on the received instruction, in which the instruction, within the created block, is transmitted for verification by the distinct computing devices.

17. One or more hardware-based non-transitory computer-readable memory devices disposed in a medical device, the computer-readable instructions, when executed by one or more processors, cause the medical device to:
- instantiate a blockchain application, in which the blockchain application is configured to enable creation of blocks on a blockchain;
- receive an instruction to operate the medical device, in which the instruction includes modifying one or more operational components of the medical device from a previous treatment;
- accept and execute the received instruction to modify the one or more operational components at the medical device responsive to a consensus being formed within a blockchain, wherein executing includes modifying a mechanism at the medical device;
- receive a subsequent to operate the medical device, in which the subsequent instruction includes operating one or more components of the medical device or modifying one or more operational components of the medical device; and
- reject the received subsequent instruction at the medical device responsive to the consensus not being formed within the blockchain.

18. The one or more hardware-based non-transitory memory devices of claim 17, wherein the medical device is a hemodialysis machine.

19. The one or more hardware-based non-transitory memory devices of claim 18, wherein the executed instructions further cause the medical device to:
- responsive to receiving the instruction, transmit the instruction to one or more other distinct medical devices, wherein the distinct medical devices verify the instruction; and
- receive the consensus from the distinct medical devices.

20. The one or more hardware-based non-transitory memory devices of claim 18, wherein patient information in the instruction is anonymized.

* * * * *